United States Patent
Donnet

(10) Patent No.: US 12,241,121 B2
(45) Date of Patent: Mar. 4, 2025

(54) METHODS, SYSTEMS, AND COMPUTER-READABLE MEDIA FOR ACCELERATED BASE CALLING

(71) Applicant: LIFE TECHNOLOGIES CORPORATION, Carlsbad, CA (US)

(72) Inventor: Benjamin Donnet, Wynnum (AU)

(73) Assignee: Life Technologies Corporation, Carlsbad, CA (US)

(*) Notice: Subject to any disclaimer, the term of this patent is extended or adjusted under 35 U.S.C. 154(b) by 1312 days.

(21) Appl. No.: 15/929,970

(22) Filed: Jun. 1, 2020

(65) Prior Publication Data

US 2020/0407784 A1 Dec. 31, 2020

Related U.S. Application Data

(62) Division of application No. 14/880,439, filed on Oct. 12, 2015, now Pat. No. 10,676,787.

(60) Provisional application No. 62/063,124, filed on Oct. 13, 2014.

(51) Int. Cl.
C12Q 1/6869 (2018.01)
G16B 25/00 (2019.01)

(52) U.S. Cl.
CPC ........... C12Q 1/6869 (2013.01); G16B 25/00 (2019.02)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,210,015 A | 5/1993 | Gelfand et al. |
| 5,399,491 A | 3/1995 | Kacian et al. |
| 5,587,128 A | 12/1996 | Wilding et al. |
| 5,750,341 A | 5/1998 | Macevicz |
| 5,854,033 A | 12/1998 | Lizardi |
| 6,033,546 A | 3/2000 | Ramsey |
| 6,054,034 A | 4/2000 | Soane et al. |
| 6,174,670 B1 | 1/2001 | Wittwer et al. |
| 6,210,891 B1 | 4/2001 | Nyren et al. |
| 6,258,568 B1 | 7/2001 | Nyren |
| 6,274,320 B1 | 8/2001 | Rothberg et al. |
| 6,399,952 B1 | 6/2002 | Maher et al. |
| 6,404,907 B1 | 6/2002 | Gilchrist et al. |
| 6,613,525 B2 | 9/2003 | Nelson et al. |
| 6,780,591 B2 | 8/2004 | Williams et al. |
| 6,828,100 B1 | 12/2004 | Ronaghi |
| 6,833,246 B2 | 12/2004 | Balasubramanian |
| 6,911,327 B2 | 6/2005 | McMillan et al. |
| 6,960,437 B2 | 11/2005 | Enzelberger et al. |
| 7,037,687 B2 | 5/2006 | Williams et al. |
| 7,049,645 B2 | 5/2006 | Sawada et al. |
| 7,133,782 B2 | 11/2006 | Odedra |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,323,305 B2 | 1/2008 | Leamon et al. |
| 7,335,762 B2 | 2/2008 | Rothberg et al. |
| 7,348,181 B2 | 3/2008 | Walt et al. |
| 7,424,371 B2 | 9/2008 | Kamentsky |
| 7,535,232 B2 | 5/2009 | Barbaro et al. |
| 7,575,865 B2 | 8/2009 | Leamon et al. |
| 7,645,596 B2 | 1/2010 | Williams et al. |
| 7,782,237 B2 | 8/2010 | Ronaghi et al. |
| 7,785,862 B2 | 8/2010 | Kim et al. |
| 7,835,871 B2 | 11/2010 | Kain et al. |
| 7,875,440 B2 | 1/2011 | Williams et al. |
| 7,948,015 B2 | 5/2011 | Rothberg et al. |
| 8,594,951 B2 | 11/2013 | Homer |
| 8,666,678 B2 | 3/2014 | Davey et al. |
| 9,388,462 B1 | 7/2016 | Eltoukhy |
| 2003/0219797 A1 | 11/2003 | Zhao et al. |
| 2004/0018506 A1 | 1/2004 | Koehler et al. |
| 2004/0197793 A1 | 10/2004 | Hassibi et al. |
| 2004/0197845 A1 | 10/2004 | Hassibi et al. |
| 2005/0084851 A1 | 4/2005 | Ronaghi et al. |
| 2006/0040297 A1 | 2/2006 | Leamon et al. |

(Continued)

FOREIGN PATENT DOCUMENTS

GB 2461127 A 12/2009
WO WO-03020895 A2 3/2003

(Continued)

OTHER PUBLICATIONS

Al Tera, "Enabling High-Performance DSP Applications with Stratix V Variable-Precision DSP Blocks," Altera Corporation, White Paper WP-01131-1.1 (available at https://www.altera.com/contentldam/altera-www/global/en_US/pdfs/literature/wp/wp-0 1131-stxvdsp-architecture.pdf (last visited Oct. 7, 2016) (document dated May 2011).

Al Tera, "Introducing Innovations at 28 nm to Move Beyond Moore's Law," Altera Corporation, White Paper WP-01125-1.2 (available at https://www.altera.com/content/dam/alterawww/global/en_US/pdfs/literature/wp/wp-01125-stxv-28nm-innovation.pdf (last visited Oct. 6, 2016) (document dated Jun. 2012).

Bartholoma et al., "Implementing Signal Processing Algorithms on FPGAs," University of Applied Sciences Pforzheim, Germany, available at http://citeseerx.ist.psu.edu/viewdoc/download?doi=1 0.1.1.130.8731 &rep=rep1 &type=pdf ,4 pgs (available online at least as early as Oct. 12, 2014; last visited Oct. 6, 2016).

(Continued)

Primary Examiner — Joseph Woitach

(57) ABSTRACT

Embodiments disclose methods, systems, and computer-readable media for accelerated base calling of sequencing data. These methods may be adapted to accelerate sequence determination for data arising from a variety of different nucleic acid sequencing platforms. In various embodiments, configurable logic circuits such as FPGAs and GPUs may be adapted to perform raw signal processing, basecalling, and/or sequence determination operations providing further enhancements to the sequence analysis methods.

19 Claims, 15 Drawing Sheets

Specification includes a Sequence Listing.

(56) References Cited

U.S. PATENT DOCUMENTS

| | | |
|---|---|---|
| 2006/0147935 A1 | 7/2006 | Linnarsson |
| 2006/0147983 A1 | 7/2006 | O'Uchi |
| 2007/0059733 A1 | 3/2007 | Sundararajan et al. |
| 2007/0059741 A1 | 3/2007 | Kamahori et al. |
| 2007/0092872 A1 | 4/2007 | Rothberg et al. |
| 2007/0207471 A1 | 9/2007 | Osaka et al. |
| 2007/0219367 A1 | 9/2007 | Shchepinov et al. |
| 2007/0281300 A1 | 12/2007 | Russell et al. |
| 2008/0166727 A1 | 7/2008 | Esfandyarpour et al. |
| 2008/0182757 A1 | 7/2008 | Heiner et al. |
| 2008/0286762 A1 | 11/2008 | Miyahara et al. |
| 2008/0286767 A1 | 11/2008 | Miyahara et al. |
| 2009/0024331 A1 | 1/2009 | Tomaney et al. |
| 2009/0026082 A1 | 1/2009 | Rothberg et al. |
| 2009/0053724 A1 | 2/2009 | Roth et al. |
| 2009/0105959 A1 | 4/2009 | Braverman et al. |
| 2009/0127589 A1 | 5/2009 | Rothberg et al. |
| 2009/0137404 A1 | 5/2009 | Drmanac et al. |
| 2009/0176200 A1 | 7/2009 | Wakita et al. |
| 2010/0035252 A1 | 2/2010 | Rothberg et al. |
| 2010/0075327 A1 | 3/2010 | Maxham et al. |
| 2010/0088255 A1 | 4/2010 | Mann |
| 2010/0105052 A1 | 4/2010 | Drmanac et al. |
| 2010/0137143 A1 | 6/2010 | Rothberg et al. |
| 2010/0159461 A1 | 6/2010 | Toumazou et al. |
| 2010/0160172 A1 | 6/2010 | Erlich et al. |
| 2010/0173303 A1 | 7/2010 | Ronaghi et al. |
| 2010/0188073 A1 | 7/2010 | Rothberg et al. |
| 2010/0192032 A1 | 7/2010 | Chen et al. |
| 2010/0197507 A1 | 8/2010 | Rothberg et al. |
| 2010/0199155 A1 | 8/2010 | Kermani et al. |
| 2010/0209922 A1 | 8/2010 | Williams et al. |
| 2010/0267043 A1 | 10/2010 | Braverman et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304447 A1 | 12/2010 | Harris |
| 2010/0323348 A1 | 12/2010 | Hamady et al. |
| 2010/0323350 A1 | 12/2010 | Gordon et al. |
| 2011/0183320 A1 | 7/2011 | Flusberg et al. |
| 2011/0213563 A1 | 9/2011 | Chen et al. |
| 2011/0230358 A1 | 9/2011 | Rava |
| 2011/0246084 A1 | 10/2011 | Ronaghi et al. |
| 2011/0257889 A1 | 10/2011 | Klammer et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0294115 A1 | 12/2011 | Williams et al. |
| 2012/0035062 A1 | 2/2012 | Schultz et al. |
| 2012/0037961 A1 | 2/2012 | Rothberg et al. |
| 2012/0040844 A1 | 2/2012 | Rothberg et al. |
| 2012/0109598 A1 | 5/2012 | Davey et al. |
| 2012/0172241 A1 | 7/2012 | Rearick et al. |
| 2012/0173158 A1 | 7/2012 | Hubbell |
| 2012/0173159 A1 | 7/2012 | Davey et al. |
| 2013/0060482 A1 | 3/2013 | Sikora et al. |
| 2013/0090860 A1 | 4/2013 | Sikora et al. |
| 2014/0051584 A1 | 2/2014 | Davey et al. |
| 2014/0220558 A1 | 8/2014 | Homer et al. |
| 2014/0222399 A1 | 8/2014 | Davey et al. |
| 2014/0316716 A1 | 10/2014 | Jiang et al. |

FOREIGN PATENT DOCUMENTS

| | | |
|---|---|---|
| WO | WO-2004001015 A2 | 12/2003 |
| WO | WO-2007098049 A2 | 8/2007 |
| WO | WO-2009117119 A1 | 9/2009 |
| WO | WO-2009158006 A2 | 12/2009 |
| WO | WO-2010047804 A1 | 4/2010 |
| WO | WO-2010077859 A2 | 7/2010 |
| WO | WO-2010138182 A2 | 12/2010 |

OTHER PUBLICATIONS

Eltoukhy, H., et al., "Modeling and Base-Calling for DNA Sequencing-By-Synthesis", 2006 IEEE International Conference on Acoustics, Speech, and Signal Processing, vol. 2, May 2006, II-1032-II-1035.

Fabian Menges et al., "Improved Accuracy and Performance via Integrated Alignment and Base-Calling," Bioinformatics, Jun. 30, 2011, vol. 27, No. 17, pp. 2330-2337.

Gallagher, "Mapping DSP Algorithms Into FPGAs, " Xilinx, Inc., available at http://www.ieee.li/pdf/viewgraphs/mapping_dsp_algorithms_into_fpgas.pdf, 35 pgs (available online at least as early as Oct. 12, 2014; last visited Oct. 6, 2016).

Ji et al., "BM-BC: A Bayesian method of base calling for Solexa sequence data," BMC Bioinformatics, 13(Suppl 13):S6, 1-9 (2012).

Kao et al., "BayesCall: A model-based base-calling algorithm for high-throughput short-read sequencing," Genome Research, vol. 19, No. 10, Oct. 2009, 1884-1895.

Leamon et al., "Cramming More Sequencing Reactions onto Microreactor Chips", Chemical Reviews, vol. 107, No. 8, Aug. 2007, pp. 3367-3376.

Ledergerber et al., "Base-calling for next-generation sequencing platforms," Briefings in Bioinformatics Advance Access, 12(5):489-497 (Jan. 18, 2011 ).

Margulies et al., "Genome Sequencing in Microfabricated High-Density Picolitre Reactors", Nature, vol. 437, No. 15, 2005, pp. 376-380.

Margulies et al., "Supplemental Materials, Genome Sequencing in Microfabricated High-Density Picolitre Reactors", Nature, vol. 437, No. 15, 2005, pp. 1-34.

Massingham et al., "All Your Base: a fast and accurate probabilistic approach to base calling," Genome Biology, 13:R13, 1-15 (2012).

Pourmand et al., "Direct electrical detection of DNA synthesis", Proceedings of the National Academy of Sciences, vol. 103, No. 17, Apr. 2006, pp. 6466-6470.

Ronaghi et al., "A Sequencing Method Based on Real-Time Pyrophosphate", Science, vol. 281, No. 5375, Jul. 1998, pp. 363-365.

Ronaghi, "Pyrosequencing Sheds Light on DNA Sequencing," Genome Research, 11:3-11 (2001).

Svantesson et al., "A mathematical model of the Pyrosequencing reaction system," Biophysical Chemistry, 100:129-145 (2004).

METHODS, SYSTEMS, AND COMPUTER-READABLE MEDIA FOR ACCELERATED BASE CALLING

CROSS-REFERENCE TO RELATED APPLICATIONS

This application is a division of U.S. application Ser. No. 14/880,439 filed Oct. 12, 2015, which claims priority to U.S. application No. 62/063,124 filed Oct. 13, 2014, which disclosures are herein incorporated by reference in their entirety.

SEQUENCE LISTING

The instant application contains a Sequence Listing which has been submitted electronically in ASCII format and is hereby incorporated by reference in its entirety. Said ASCII copy, created on Sep. 14, 2020, is named LT00981DIV_SL.txt and is 829 bytes in size.

FIELD OF THE DISCLOSURE

The disclosure relates generally to computing methods, apparatus, and systems for biological data analysis, more specifically, the disclosure relates to technologies for processing data from nucleic acid sequencing instruments.

BACKGROUND

Emerging instruments and technologies for nucleic acid sequencing and genetic analysis continue to revolutionize many aspects of biology and medicine. Sequencing costs have steadily declined in recent years while the overall instrument throughput has increased dramatically. These improvements have made it possible to apply sequencing technology to a wide variety of disparate fields.

Current sequencing technologies generate data for many nucleic acid (e.g. DNA and RNA) fragments sequenced in parallel. Oftentimes, large strands of genetic material are broken or separated into comparatively short DNA fragments, and the nucleotide sequence of these DNA fragments is desirably determined. An important step to elucidate the actual nucleic acid sequence for each of these fragments involves "basecalling."

Basecalling resolves signal information generated by a sequencing instrument and identifies candidate nucleotide or base identifications from the data. Resolving and assembling the fragment sequences from next generation sequencing data presents a particular challenge in terms of obtaining timely results. Modern high throughput sequencing instruments are capable of generating data for many millions of bases (or more) per day.

A significant bottleneck in the sequencing workflow arises in association with the processing of data from the sequencing instrument. Actual sequence data may not available for hours or days after a sequencing run has been completed because of the time required to resolve the raw signal data using complex computational pipelines.

Despite the availability of high speed computing platforms, raw signal processing and data analysis continues to be a limiting factor in the time-to-result for sequencing samples for high throughput next generation sequencing platforms. This can pose a particular problem, for example, in clinical applications where medical diagnosis and decisions cannot be rendered until the sample data analysis is completed.

It is thus desirable to develop improved analysis techniques capable of processing large amounts of sequence data. A goal of at least certain methods discussed in detail below, among others, is to provide technologies and analysis workflows capable of efficiently handling and resolving sequencing instrument data in a timely manner. This goal may be achieved by implementing the processing techniques described below. As a result, the efficiency and speed of data analysis may be substantially improved over existing methods.

SUMMARY OF THE DISCLOSURE

Embodiments disclose methods, systems, and computer-readable media for accelerated base calling of sequencing data. These methods may be adapted to accelerate sequence determination for data arising from a variety of different instrument nucleic acid sequencing platforms. In various embodiments, configurable logic circuits such as FPGAs may be adapted to perform raw signal processing, basecalling, and/or sequence determination operations providing further enhancements to analysis methods. While disclosed in the context of nucleic acid sequencing data resolution and analysis, it will be appreciated that the methods and hardware configurations described herein may be adapted for use with many types of biological data including, for example, DNA, RNA, and protein sequencing signal information and data.

According to certain embodiments, computer-implemented methods are disclosed for processing raw sequence information or signal data arising from a sequencing instrument. The data may further take many forms determined in part by the type of sequencing technology used. For example, label-based methods for sequence analysis may produce data reflecting signal intensities captured from fluorescent markers or radiolabeled molecules. Alternatively, unlabeled methods for sequence analysis may generate data reflecting detected changes in pH or hydrogen ion concentration.

Analysis of sequencing data may involve evaluation of instrument sample signal information and performing multiple candidate nucleotide identifications or "basecalls." Bases or nucleotides may be identified by comparing the likelihood or confidence in various putative identifications. Conventionally, such processes are highly iterative and may take significant computing resources and time to complete. A single sample analysis may require millions, billions, or more of discrete base identifications, each with demanding computational requirements. Due in part, to the often extreme size of a sample data set, inefficiencies in algorithmic design and/or limited computational power of the hardware used to process the signal data can result in performance bottlenecks leading to long processing times and delayed results.

According to various embodiments, a method is disclosed for sample nucleotide sequence determination wherein the method comprises (a) flowing nucleotides onto a sensor array adapted for sequencing, the sensor array including a first well containing a sample polynucleotide, (b) receiving from the sensor array, signal data relating to chemical reactions resulting from the flow of nucleotides, the signal data including a phase-synchrony error component, (c) processing the signal data using a hardware-embedded basecaller that identifies putative basecalls corresponding to a nucleotide sequence for the sample polynucleotide using a plurality of parallel channels, each channel processing a selected nucleotide identification hypothesis using a normalization module to identify gain and offset associated with the phase-synchrony error component of the signal data generating normalized signal data, and a solver module that further evaluates the normalized signal data and identifies a putative basecall corresponding to the normalized signal data, (d) generating from the putative basecalls, a resulting nucleotide identification with the highest confidence of being attributable to a select nucleotide flow, (e) repeating steps (c)-(d) such that for each iteration of the basecaller the nucleotide sequence of the sample polynucleotide is extended by at least one nucleotide; and (f) outputting the resulting identified nucleotide sequence for the sample polynucleotide.

According to other embodiments, a system is disclosed for sample nucleotide sequence determination comprising: a sensor array adapted for sequencing, the sensor array including a first well containing a sample polynucleotide and configured to receive a plurality of flows of nucleotides; a signal data processor that receives signal data from the sensor array, the signal data resultant from chemical reactions associated with the flow of nucleotides and including a phase-synchrony error component; a basecall processor that receives signal data from the signal data processor and identifies putative basecalls corresponding to a nucleotide sequence for the sample polynucleotide using a plurality of parallel channels, wherein each channel further comprises (a) a normalization component that processes a selected nucleotide identification hypothesis identifying gain and offset associated with the phase-synchrony error component of the signal data generating normalized signal data, (b) a solver component that further evaluates the normalized signal data and identifies a putative basecall corresponding to the normalized signal data, and (c) a best candidate selector that generates a resulting nucleotide identification with the highest confidence of being attributable to a select nucleotide flow; and a data output module that assembles the resulting nucleotide identifications and outputs an identified nucleotide sequence for the sample polynucleotide.

The system may further include use of a normalization component comprising a plurality of windowed normalizers, each processing discrete nucleotide identification hypothesis in parallel. Additionally, the system may provide a basecaller processor comprising a plurality of programmable electronic circuits implementing logic for the normalization component and the solver component. The basecall processor of the system may comprise a discrete component receiving signal data generated by at least one sequencing instrument and outputting the identified nucleotide sequence for the sample polynucleotide to be processed by at least one data analysis server. The sensor array of the system may comprise a plurality of wells each containing discrete sample polynucleotides. The signal data of the system may be indicative of chemical reactions associated with a collection of discrete sample polynucleotides that are processed in parallel by the basecall processor.

According to still further embodiments, a sequence determination apparatus is disclosed comprising: a basecall processor that receives signal data from a sequencing instrument and identifies putative basecalls corresponding to a nucleotide sequence for a sample polynucleotide contained in a first well of a sensor array associated with the sequencing instrument wherein the signal data results from chemical reactions that take place for a plurality of flows of nucleotides into the first well during sequencing on the sequencing instrument; a plurality of parallel channels implemented as a plurality of logic gates within the basecall processor, each channel comprising: (a) a normalization component that processes a selected nucleotide identification hypothesis identifying gain and offset associated with the phase-synchrony error component of the signal data generating normalized signal data, (b) a solver component that further evaluates the normalized signal data and identifies a putative basecall corresponding to the normalized signal data, and (c) a best candidate selector that generates a resulting nucleotide identification with the highest confidence of being attributable to a select nucleotide flow; and a data output module that assembles the resulting nucleotide identifications and outputs an identified nucleotide sequence for the sample polynucleotide.

The apparatus may further include a normalization component that applies a single-pass, non-iterative approximation of gain and offset associated with the phase-synchrony error component of the signal data. Additionally, the normalization component may comprise a plurality of windowed normalizers, each processing discrete nucleotide identification hypothesis in parallel. The apparatus may also implement a basecall processor that receives signal data generated by at least one sequencing instrument associated with the sequencing system and outputs the identified nucleotide sequence for the sample polynucleotide. The sensor array of the apparatus may comprise a plurality of wells each containing discrete sample polynucleotides. The signal data of the apparatus may be indicative of chemical reactions associated with a collection of discrete sample polynucleotides that are processed in parallel by the basecall processor.

According to certain embodiments, improved methods for performing sequence signal processing and basecalls are disclosed. These methods are adaptable to specialized hardware platforms capable of being programmed to operate as dedicated data processing engines with much greater efficiency than may be achieved using software running in typical general purpose computing platforms and distributed systems. Such methods may be applied, for example, to raw signal data generated by sequencing instruments performing sequencing-by-synthesis.

According to certain embodiments, non-transitory computer readable media are disclosed that store instructions that, when executed by a computer, cause the computer to perform accelerated methods for base calling of sequencing data.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the scope of disclosed embodiments, as set forth by the claims.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 4 discloses SEQ ID NO: 2.

DETAILED DESCRIPTION OF EMBODIMENTS

Figure 1:
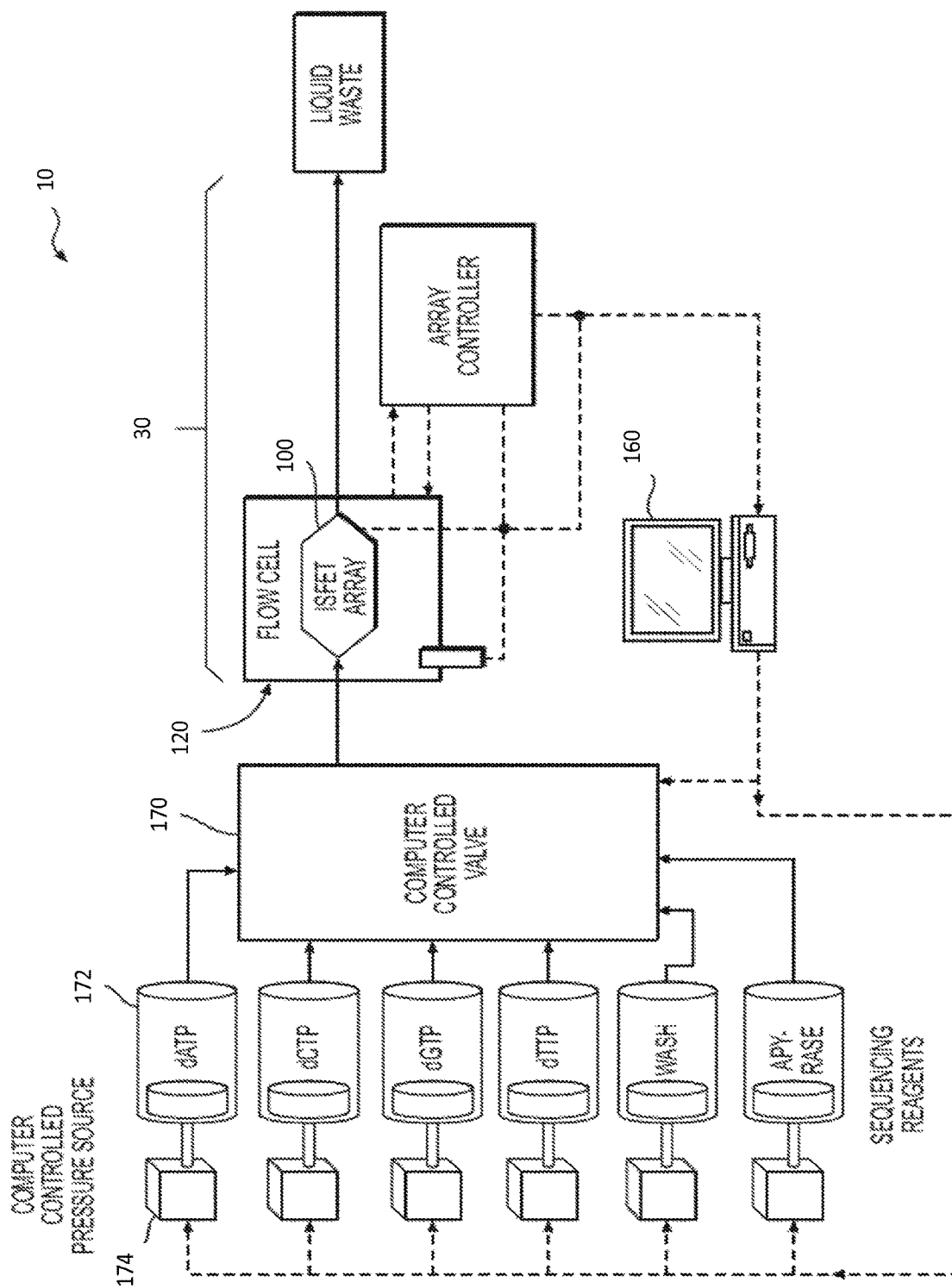
FIG. 1 depicts a nucleic acid processing system including a large scale chemFET array, according to exemplary embodiments of the present disclosure.

The following description of various exemplary embodiments is exemplary and explanatory only and is not to be construed as limiting or restrictive in any way. Other embodiments, features, objects, and advantages of the present disclosure will be apparent from the description and accompanying drawings, and from the claims.

In accordance with the disclosure and principles embodied in this application, new methods, systems, and computer readable media for making basecalls by processing and analyzing signal information/data that allow high-throughput identification of nucleic acid sequences with increased accuracy, speed, and/or efficiency. In particular, the present disclosure enable rapid deconvolution of large amounts of sequence data (for example, in the form of raw signal information) to accurately identify correct basecalls in the presence of systematic errors, signal artifacts, weak incorporations signals and/or inefficiencies in the underlying sequencing chemistry. The methods described herein are also well suited for resolving basecalls where sequencing effects and artifacts (such as, e.g., phasing effects) are present. These effects may increase as a function of the sample template read lengths increasing the difficulty in making accurate basecalls.

Exemplary embodiments of the present disclosure relate in part to the use of large arrays of chemically sensitive field effect transistors ("chemFETs"), and more particularly to ion-sensitive field effect transistors ("ISFETs"), which monitor reactions, including for example nucleic acid (e.g., RNA and DNA) sequencing reactions, by monitoring analytes present, generated, and/or used during a reaction.

Various technologies and platforms exist for performing nucleic acid sequencing and each of these platforms generate large volumes of sequencing data including. Commercially available sequencing instruments include, the Genome Analyzer/HiSeq/MiSeq platforms (Illumina, Inc.; see, e.g., U.S. Pat. Nos. 6,833,246 and 5,750,341); the GS FLX, GS FLX Titanium, and GS Junior platforms (Roche/454 Life Sciences; see, e.g., Ronaghi et al., SCIENCE, 281:363-365 (1998), and Margulies et al., NATURE, 437:376-380 (2005)); and the Ion Personal Genome Machine (PGM™) (Life Technologies Corp./Ion Torrent; see, e.g., U.S. Pat. No. 7,948,015 and U.S. Pat. Appl. Publ. Nos. 2010/0137143, 2009/0026082, and 2010/0282617). Each of these instruments typically generate sequencing signal data having particular characteristics and error modes that must be resolved in order to accurately identify the nucleotide bases associated with the sequencing signal data. The amount of data generated during a single sequencing run using any next generation sequencing instrument, including those identified above, can include discrete sequencing signals from independent reactions on the order of millions, tens of millions, or more of that must be quickly and accurately analyzed and resolved. A principal operation in the data analysis workflows for these instruments is processing signal information arising during a given sequencing run and transforming this data into basecalls representative of the underlying template sequence that was detected by the instrument. Before subsequent steps of analysis including fragment alignment, mutation or single polymorphism identification, organism identification, or other clinical and research evaluations may proceed, the transformation of the "raw" sequencing data into base identifications must be accomplished and therefore represents an early gating step in the sequencing workflow.

It will be appreciated that the system and methods described herein may be applied to various instruments, apparatuses, and/or systems for sequencing nucleic acids that generate large volumes of data that may need to be processed and/or analyzed. Such instruments, apparatuses, and/or systems may include, for example, the Genome Analyzer/HiSeq/MiSeq platforms (Illumina, Inc.; see, e.g., U.S. Pat. Nos. 6,833,246 and 5,750,341); the GS FLX, GS FLX Titanium, and GS Junior platforms (Roche/454 Life Sciences; see, e.g., Ronaghi et al., SCIENCE, 281:363 (1998), and Margulies et al., NATURE, 437:376-380 (2005)); and the Ion Personal Genome Machine (PGM™) (Life Technologies Corp./Ion Torrent; see, e.g., U.S. Pat. Appl. Publ. No. 2010/0137143 and No. 2009/0026082, which are both incorporated by reference herein in their entirety).

In order to increase an overall throughput of nucleic acid sequencing, among other objectives, there is a need for new methods, systems, and computer readable media that allow increases in accuracy, speed, and/or efficiency of processing and/or analyzing of large volumes of nucleic acid sequencing data and/or signals. In accordance with the disclosure and principles embodied in this application, new methods, systems, and computer readable media for processing and/or analyzing data and/or signals to accurately resolve high-throughput sequence data using modified hardware solutions capable of processing sequencing data using methods that substantially reduce the number of computational clock cycles required for each round of nucleotide identification or basecalling. Implemented in connection with specialized hardware solutions such as FPGA and GPU processors further increases the speed, and/or efficiency of sequence identification relative to conventional general purpose computing software applications.

In this application, "amplifying" generally refers to performing an amplification reaction. In this application, "amplicon" generally refers to a product of a polynucleotide amplification reaction, which includes a clonal population of polynucleotides, which may be single stranded or double stranded and which may be replicated from one or more starting sequences. The one or more starting sequences may be one or more copies of the same sequence, or they may be a mixture of different sequences that contain a common region that is amplified such as, for example, a specific exon sequence present in a mixture of DNA fragments extracted from a sample. Preferably, amplicons may be formed by the amplification of a single starting sequence. Amplicons may be produced by a variety of amplification reactions whose products comprise replicates of one or more starting, or target, nucleic acids. Amplification reactions producing amplicons may be "template-driven" in that base pairing of reactants, either nucleotides or oligonucleotides, have complements in a template polynucleotide that are required for the creation of reaction products. Template-driven reactions may be primer extensions with a nucleic acid polymerase or oligonucleotide ligations with a nucleic acid ligase. Such reactions include, for example, polymerase chain reactions (PCRs), linear polymerase reactions, nucleic acid sequence-based amplifications (NASBAs), rolling circle amplifications, for example, including such reactions disclosed in the following references, which are all incorporated by reference herein in their entirety: Gelfand et al., U.S. Pat. No. 5,210,015; Kacian et al., U.S. Pat. No. 5,399,491; Mullis, U.S. Pat. No. 4,683,202; Mullis et al., U.S. Pat. Nos. 4,683,195; 4,965,188; and 4,800,159; Lizardi, U.S. Pat. No. 5,854,033; and Wittwer et al., U.S. Pat. No. 6,174,670. In an exemplary embodiment, amplicons may be produced by PCRs. Amplicons may also be generated using rolling circle amplification to form a single body that may exclusively occupy a microwell as disclosed in Drmanac et al., U.S. Pat. Appl. Publ. No. 2009/0137404, which is incorporated by reference herein in its entirety.

In this application, "solid phase amplicon" generally refers to a solid phase support, such as a particle or bead, to which is attached a clonal population of nucleic acid sequences, which may have been produced by a process such as emulsion PCR, or like technique, for example.

In this application, "analyte" generally refers to a molecule or biological cell that can directly affect an electronic sensor at a sample retaining region (such as a defined space or reaction confinement region or microwell, for example) or that can indirectly affect such an electronic sensor by a by-product from a reaction involving such molecule or biological cell located in such a sample retaining region. In an exemplary embodiment, an analyte may be a sample or template nucleic acid, which may be subjected to a sequencing reaction, which may, in turn, generate a reaction by-product, such as one or more hydrogen ions, that can affect an electronic sensor. The term "analyte" also comprehends multiple copies of analytes, such as proteins, peptides, nucleic acids, or the like, attached to solid supports, such as beads or particles, for example. In an exemplary embodiment, an analyte may be a nucleic acid amplicon or a solid phase amplicon. A sample nucleic acid template may be associated with a surface via covalent bonding or a specific binding or coupling reaction, and may be derived from, for example, a shot-gun fragmented DNA or amplicon library (which are examples of library fragments further discussed herein), or a sample emulsion PCR process creating clonally-amplified sample nucleic acid templates on particles such as IonSphere™ particles. An analyte may include particles having attached thereto clonal populations of DNA fragments, e.g., genomic DNA fragments, cDNA fragments, or the like.

In this application, "primer" generally refers to an oligonucleotide, either natural or synthetic, that is capable, upon forming a duplex with a polynucleotide template, of acting as a point of initiation of nucleic acid synthesis and being extended from its 3' end along the template so that an extended duplex may be formed. Extension of a primer may be carried out with a nucleic acid polymerase, such as a DNA or RNA polymerase. The sequence of nucleotides added in the extension process is determined by the sequence of the template polynucleotide. Usually primers are extended by a DNA polymerase. Primers may have a length in the range of from 14 to 40 nucleotides, or in the range of from 18 to 36 nucleotides, for example, or from N to M nucleotides where N is an integer larger than 18 and M is an integer larger than N and smaller than 36, for example. Other lengths are of course possible.

In this application, "oligonucleotide" generally refers to a linear polymer of nucleotide monomers and may be DNA or RNA. Monomers making up polynucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g., naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. In an exemplary embodiment, oligonucleotide may refer to smaller polynucleotides, for example, having 5-40 monomeric units. Polynucleotides may comprise the natural deoxynucleosides (e.g., deoxyadenosine, deoxycytidine, deoxyguanosine, and deoxythymidine for DNA or their ribose counterparts for RNA) linked by phosphodiester linkages. However, they may also comprise non-natural nucleotide analogs, e.g., including modified bases, sugars, or internucleosidic linkages. In an exemplary embodiments, a polynucleotide may be represented by a sequence of letters (upper or lower case), such as "ATGCCTG," and it will be understood that the nucleotides are in 5'→3' order from left to right and that "A" denotes deoxyadenosine, "C" denotes deoxycytidine, "G" denotes deoxyguanosine, and "T" denotes thymidine, and that "I" denotes deoxyinosine, and "U" denotes deoxyuridine, unless otherwise indicated or obvious from context.

In this application, "defined space" (or "reaction space," which may be used interchangeably with "defined space") generally refers to any space (which may be in one, two, or three dimensions) in which at least some of a molecule, fluid, and/or solid can be confined, retained and/or localized. The space may be a predetermined area or volume, and may be defined, for example, by a depression or a micro-machined well in or associated with a microwell plate, microtiter plate, microplate, or a chip. The area or volume may also be determined based on an amount of fluid or solid, for example, deposited on an area or in a volume otherwise defining a space. For example, isolated hydrophobic areas on a generally hydrophobic surface may provide defined spaces. In an exemplary embodiment, a defined space may be a reaction chamber, such as a well or a microwell, which may be in a chip. A defined space may contain or be exposed to enzymes and reagents used in nucleotide incorporation.

In this application, "reaction confinement region" generally refers to any region in which a reaction may be confined and includes, for example, a "reaction chamber," a "well," and a "microwell" (each of which may be used interchangeably). A reaction confinement region may include a region in which a physical or chemical attribute of a solid substrate can permit the localization of a reaction of interest, and a discrete region of a surface of a substrate that can specifically bind an analyte of interest (such as a discrete region with oligonucleotides or antibodies covalently linked to such surface), for example. Reaction confinement regions may be hollow or have well-defined shapes and volumes, which may be manufactured into a substrate. These latter types of reaction confinement regions are referred to herein as microwells or reaction chambers, and may be fabricated using any suitable microfabrication techniques. Reaction confinement regions may be arranged as an array, which may be a substantially planar one-dimensional or two-dimensional arrangement of elements such as sensors or wells.

The number of columns (or rows) of a two-dimensional array may or may not be the same. Preferably, the array comprises at least 100,000 chambers. Preferably, each reaction chamber has a horizontal width and a vertical depth that has an aspect ratio of about 1:1 or less. Preferably, the pitch between the reaction chambers is no more than about 10 microns. Preferably, each reaction chamber is no greater than 0.34 µL, and more preferably no greater than 0.096 µL or even 0.012 µL in volume. Microwells may have any polygonal cross sections, including square, rectangular, or octagonal cross sections, for example, and may be arranged as a rectilinear array on a surface. Microwells may have hexagonal cross sections and be arranged as a hexagonal array, which permits a higher density of microwells per unit area than rectilinear arrays.

A plurality of defined spaces or reaction confinement regions may be arranged in an array, and each defined space or reaction confinement regions may be in electrical communication with at least one sensor to allow detection or measurement of one or more detectable or measurable parameter or characteristics. The sensors may convert changes in the presence, concentration, or amounts of reaction by-products (or changes in ionic character of reactants) into an output signal, which may be registered electronically, for example, as a change in a voltage level or a current level which, in turn, may be processed to extract information about a chemical reaction or desired association event, for example, a nucleotide incorporation event. The sensors may include at least one chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of a physical property (or a change in such value), such as an ion concentration.

An initial measurement or interrogation of a pH for a defined space or reaction confinement regions, for example, may be represented as an electrical signal or a voltage, which may be digitalized (e.g., converted to a digital representation of the electrical signal or the voltage). Any of these measurements and representations may be considered raw data or a raw signal. The structure and/or design of sensors for use with the present disclosure may vary widely and may include one or more features of the following references, which are all incorporated by reference herein in their entirety: Rothberg et al., U.S. Pat. Appl. Publ. No. 2009/0127589; Rothberg et al., U.K. Pat. Appl. No. GB24611127; Barbaro et al., U.S. Pat. No. 7,535,232; Sawada et al., U.S. Pat. No. 7,049,645; Kamahori et al., U.S. Pat. Appl. Publ. No. 2007/0059741; Miyahara et al., U.S. Pat. Appl. Publ. Nos. 2008/0286767 and 2008/0286762; O'uchi, U.S. Pat. Appl. Publ. No. 2006/0147983; Osaka et al., U.S. Pat. Appl. Publ. No. 2007/0207471; and Esfandyarpour et al., U.S. Pat. Appl. Publ. No. 2008/0166727.

In this application, "reaction mixture" generally refers to a solution containing all the necessary reactants for performing a reaction, which may include, for example, buffering agents to maintain pH at a selected level during a reaction, salts, enzymes, co-factors, scavengers, and the like, for example.

In this application, "microfluidics device" generally refers to an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls, e.g., to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device may have cross-sectional dimensions of less than a few hundred square micrometers, for example, and passages may have capillary dimensions, e.g., having maximal cross-sectional dimensions of from about 500 µm to about 0.1 µm, for example. Microfluidics devices may for example have volume capacities in the range of from 1 µL to a few nL, e.g., 10-100 nL.

In various exemplary embodiments, there are provided methods, systems, and computer readable media for processing and/or analyzing data and/or signals that allow high-throughput sequencing of nucleic acid sequences with increased accuracy, speed, and/or efficiency. The methods, systems, and computer readable media may include steps and/or structural elements for receiving raw data and/or signals, processing the raw data and/or signals using various protocols and modules, and outputting or storing any results in various formats. In an exemplary embodiment, the results may be further processed or analyzed by other methods, systems, and computer readable media.

In various exemplary embodiments, the methods, systems, and computer readable media described herein may advantageously be used to process and/or analyze data and signals obtained from pH-based nucleic acid sequencing. In pH-based sequencing, a nucleotide incorporation event may be determined by detecting hydrogen ions that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of deoxynucleoside triphosphate ("dNTP") addition (which may be referred to herein as "nucleotide flows") and washing. The primer may be annealed to the sample or template so that the primer's 3' end can be extended by a polymerase whenever dNTPs complementary to the next base in the template are added. Then, based on the known sequence of nucleotide flows and on measured signals indicative of hydrogen ion concentration during each nucleotide flow, the identity of the type, sequence and number of nucleotide(s) associated with a sample nucleic acid present in a reaction chamber can be determined Arrays including large arrays of chemFETs may be employed to detect and measure static and/or dynamic amounts or concentrations of a variety of analytes (e.g., hydrogen ions, other ions, non-ionic molecules or compounds, etc.) in a variety of chemical and/or biological processes (e.g., biological or chemical reactions, cell or tissue cultures or monitoring, neural activity, nucleic acid sequencing, etc.) in which valuable information may be obtained based on such analyte measurements. Such chemFET arrays may be employed in methods that detect analytes and/or methods that monitor biological or chemical processes via changes in charge at the chemFET surface. Accordingly, at least certain embodiments of the systems, methods, and computer-readable media discussed herein provide uses for chemFET arrays that involve detection of analytes in solution and/or detection of change in charge bound to the chemFET surface.

FIG. 1 depicts a nucleic acid processing system including a large scale chemFET array, according to exemplary embodiments of the present disclosure. An example of a nucleic acid processing system is a nucleic acid sequencing instrument such as the Ion Torrent sequencer (ThermoFisher Scientific, Carlsbad, California). The chemFET sensors of the array are described for purposes of illustration as ISFETs configured for sensitivity to static and/or dynamic ion concentration, including but not limited to hydrogen ion concentration. However, it should be appreciated that the present disclosure is not limited in this respect, and that in any of the embodiments discussed herein in which ISFETs are employed as an illustrative example, other types of chemFETs may be similarly employed in alternative embodiments. Similarly, it should be appreciated that various aspects and embodiments of the present disclosure may employ ISFETs as sensors yet detect one or more ionic species that are not hydrogen ions.

The system 10 may include a semiconductor/microfluidics hybrid structure 30 comprising an ISFET sensor array 100 and a microfluidics flow cell 120. The flow cell 120 may comprise a number of wells (not shown) disposed above corresponding sensors of the ISFET array 100. The flow cell 120 may be configured to facilitate the sequencing of one or more identical template nucleic acids disposed in the flow cell via the controlled and ordered introduction to the flow cell of a number of sequencing reagents 172 (e.g., dATP, dCTP, dGTP, dTTP (generically referred to herein as dNTP), divalent cations such as but not limited to Mg2+, wash solutions, and the like.

As illustrated in FIG. 1, the introduction of the sequencing reagents to the flow cell 120 may be accomplished via one or more valves 170 and one or more pumps 174 that are controlled by a computer 160. A number of techniques may be used to admit (i.e., introduce) the various processing materials (e.g., solutions, samples, reaction reagents, wash solutions, and the like) into the wells of such a flow cell. As illustrated in FIG. 1, reagents including dNTP may be admitted to the flow cell (e.g., via the computer controlled valve 170 and pumps 174) from which they diffuse into the wells, or reagents may be added to the flow cell by other means such as direct injection. In yet another example, the flow cell 120 may not contain any wells, and diffusion properties of the reagents may be exploited to limit cross-talk between respective sensors of the ISFET array 100, or nucleic acids may be immobilized on the surfaces of sensors of the ISFET array 100.

The flow cell 120 in the system of FIG. 1 may be configured in a variety of manners to provide one or more analytes (or one or more reaction solutions) in proximity to the ISFET array 100. For example, a template nucleic acid may be directly attached or applied in suitable proximity to one or more pixels of the sensor array 100, or in or on a support material (e.g., one or more "beads") located above the sensor array but within the reaction chambers, or on the sensor surface itself. Processing reagents (e.g., enzymes such as polymerases) may also be placed on the sensors directly, or on one or more solid supports (e.g., they may be bound to the capture beads or to other beads) in proximity to the sensors, or they may be in solution and free-flowing. It is to be understood that the device may be used without wells or beads.

In the system 10 of FIG. 1, according to one embodiment the ISFET sensor array 100 monitors ionic species, and in particular, changes in the levels/amounts and/or concentration of ionic species, including hydrogen ions. The species may be a result from a nucleic acid synthesis or sequencing reaction.

Various embodiments of the present disclosure may relate to monitoring/measurement techniques that involve the static and/or dynamic responses of an ISFET. It is to be understood that although the particular example of a nucleic acid synthesis or sequencing reaction is provided to illustrate the transient or dynamic response of chemFET, such as an ISFET, the transient or dynamic response of a chemFET, such as an ISFET, as discussed below may be exploited for monitoring/sensing other types of chemical and/or biological activity beyond the specific example of a nucleic acid synthesis or sequencing reaction.

Figure 2:
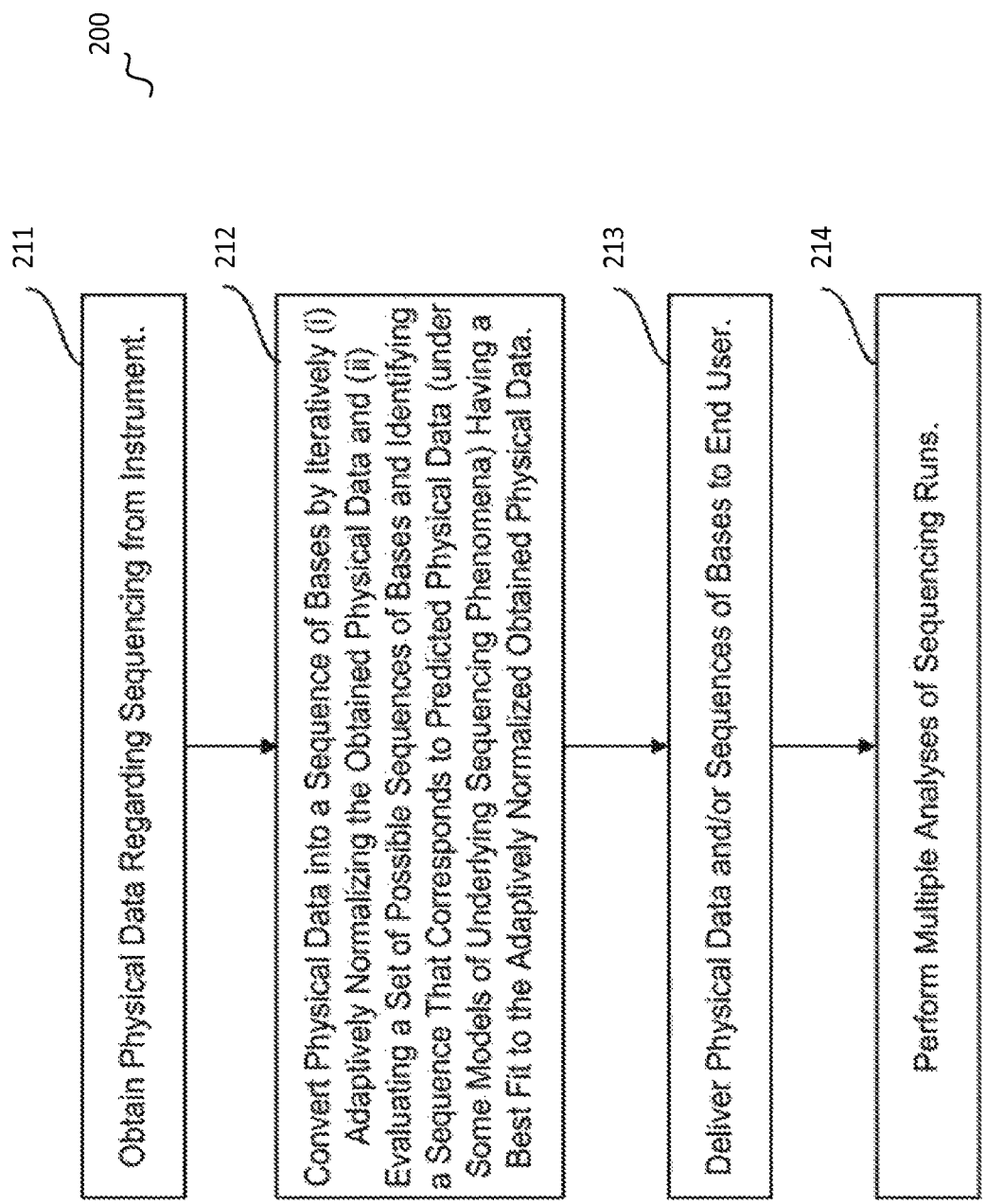
FIG. 2 depicts an exemplary embodiment of a method for sample nucleic acid data evaluation and processing.

Sequencing platforms typically apply a data analysis workflow that takes into account the characteristics and parameters required to analyze the sequencing signals arising from the instrument. As one example, the Ion Torrent platform (ThermoFisher Scientific Inc., Carlsbad, California) may be configured to perform a sequencing data analysis workflow according to the exemplary embodiment of FIG. 2. Additional details of this method may be found in U.S. patent application Ser. No. 13/645,058 (US Patent Publication 2013/0090860) Sikora et al. which is incorporated by reference in its entirety.

According to this method 200 sample nucleic acids are evaluated in a series of steps that include making base calls by processing and/or analyzing nucleic acid sequencing data. In step 211, a user obtains physical data by performing a sequencing task using a sequencing instrument. In the case on the Ion Torrent platform, the physical data may include voltage data indicative of hydrogen ion concentrations.

Nucleotide incorporation events are determined, in part, by detecting increases in hydrogen ion concentration. The signal data arising from nucleotide incorporation events detected as increased hydrogen ion concentration require processing of the signal data. In step 212, a server or other computing means or resource converts the signal data into bases sequence information by, for example, iteratively (i) adaptively normalizing the obtained signal data and (ii) evaluating a set of candidate sequences of bases and identifying a sequence that corresponds to predicted signal data (under some models of underlying sequencing phenomena) having a best fit to the adaptively normalized obtained signal data. In step 213, the server or other computing means or resource delivers the physical data and/or sequences of bases to an end user. In step 214, if many runs of physical data and/or sequences of bases have been performed, other users and/or entities may perform multiple analyses of sequencing runs. One or more of these steps and/or components may be used to perform or implement one or more aspects of the exemplary embodiments described herein.

The steps of adaptive normalization of the signal data and performing basecalling or sequence identification typically involve detailed calculations that are performed in connection with each base sequenced for each template. These steps may be further be performed by a selected nucleic acid sequencing module that is included in a sequence analysis system workflow such as that exemplified in FIG. 3 and described in greater detail hereinbelow.

Figure 3:
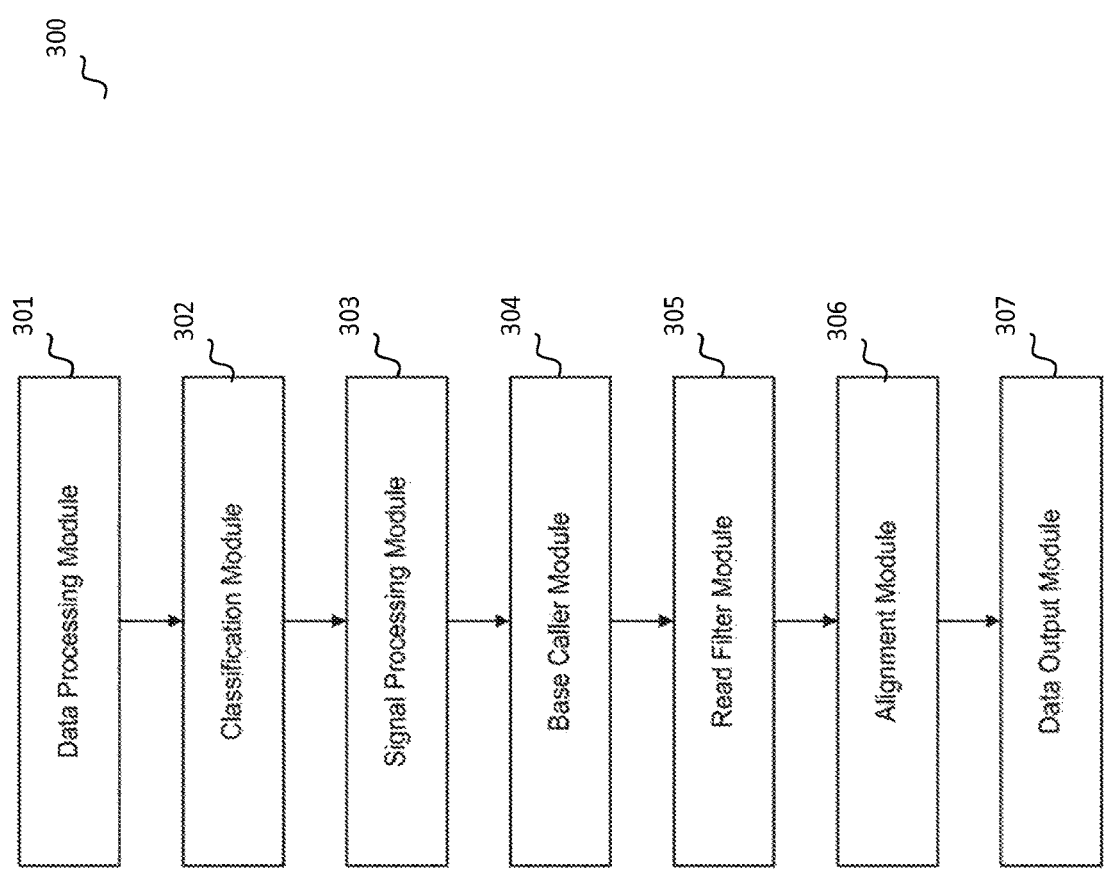
FIG. 3 depicts an exemplary embodiment comprising modules associated with a nucleic acid sequencing workflow.

In FIG. 3, the exemplary embodiment of a nucleic acid sequencing workflow 300 includes a data processing module 301, a classification module 302, a signal processing module 303, a base caller module 304, a read filter module 305, an alignment module 306, and a data output module 307. The sequencing system or platform may be implemented in one or more computers and/or servers and may be accessible at least in part through a web-accessible data portal. In an exemplary embodiment, there is provided a method performing steps including the general steps associated with modules 301-307 (e.g., processing data, classifying defined spaces or reaction confinement regions, processing signals, calling bases, filtering reads, aligning reads, and outputting results).

In an exemplary embodiment, a data processing module or data processor 301 may be configured to receive data (e.g., raw sequencing data, which may comprise a series of signals arising from various samples contained in wells), reflective or indicative of one or more by-product(s) of a chemical reaction. The signals may be derived from nucleotide incorporation events (e.g., incorporation of a dNTP associated with a sample nucleic acid template) by measuring hydrogen ions generated as by-products of polymerase-catalyzed nucleic acid extension reactions. The hydrogen ion concentration (or pH) for a defined space or reaction confinement region may be measured repeatedly and at intervals timed to coincide with the nucleotide flows of different types of dNTPs. The signals may be actual raw pH values, or they may be a conversion of the raw pH value (or related physical measurement) in each defined space into a voltage, for example, which may then be converted into a digital representation.

The data processing module 301 may be configured to generate one or more acquisition file(s) for the raw data, which may contain raw signals from defined spaces of a chip, for example, for one or more nucleotide flow(s). For a chip containing about 1.5 million wells, for example, each nucleotide flow can result in about 1.5 million separate nucleotide incorporation events, and a series of such acquisition files can represent about 1.5 million possible reads. A read can represent consecutive base calls associated with a sequence of a nucleic acid. A read can reflect bases or base complements associated with a sample nucleic acid template, which can be associated with a defined volume, such as a well, or with a defined area, such as a portion of a surface of a substantially flat substrate, for example. A read can include a full sequence of the sample nucleic acid template or a portion thereof. A read can include about eight nucleotides (base calls) and can contain 16 or more base calls, 25 or more base calls, 50 or more base calls, 100 or more base calls, or 120 or more base calls, for example. The length of a read can be expressed as a number of base pairs (bps).

In an exemplary embodiment, the data processing module 301 may be configured to perform multiple functions, including receiving or loading raw data and/or signals (which may be temporarily or permanently stored in a memory and may be compressed and decompressed as desired), decompiling raw data, and offset correcting raw data. For example, the raw data and/or signals may be streamed off of an analytical instrument directly to the data processing module. Alternatively, or in combination with direct steaming, the data processing module may access or receive the raw data and/or signals after storage or collection on a computer-readable medium, such as a portable disk or hard drive, for example. The data processing module may receive directly raw acquisition files in DAT file format (e.g., acq_*.dat files), for example, streaming from an analytical instrument.

In an exemplary embodiment, the data processing module 301 may be configured to compress data and/or signals using one or more compression modes, which may include a dynamic/variable frame rate compression mode and a key frame and/or delta compression mode. In the dynamic/variable frame rate compression mode, certain portions of a nucleotide incorporation event or a nucleotide flow may be captured at different frame rates to allow capture of biologically specific events at high resolution while reducing the overall file size by allowing multiple frames in some portions to be averaged. In the key frame and/or delta compression mode, whereas an initial value is actually stored, for subsequent values only their difference relative to the initial value may be stored.

In an exemplary embodiment, the data processing module 301 may be configured to perform raw signal offset and/or background corrections. Each defined space may have its own reference value. To compare two defined spaces, a common reference may be used. The offset and/or background correction can take the average of the first few frames within each acquisition file, and subtract that value from values for each defined space, thus allowing measurements within the defined space to have a common reference value.

In an exemplary embodiment, the data processing module 301 may flag or exclude certain defined spaces that may for whatever reason not be functional or may be covered, obscured, or otherwise fluidically inaccessible or unaddressable. For example, a mask may be loaded, per chip type, to mark those defined spaces as excluded so as to avoid unnecessary and/or computationally inefficient downstream processing of the chip and signals generated therefrom, where the information likely will be uninformative.

In an exemplary embodiment, a classification module or classifier 302 may be configured to classify one or more wells of an array as to whether the well is empty or contains an analyte or substrate associated with an analyte and whether the well generally contains useful information that should be carried forward and included in downstream processing and/or analysis. Because the data can include signals from thousands to millions of individual wells, reducing the amount of data to be carried forward can increase overall performance and efficiency, and conserve file storage space. (Of course, in practice while some data can be screened, all data may be stored so that various screening and manipulating of the data can be started anew, if desired.) The classification module 302 may process wells in smaller groups or regions rather than as one group to exploit parallel computing techniques, such as multi-core and/or multi-process nodes that have parallel computational capabilities. For example, a chip containing an array of about 1.5 million wells can be segmented into 50×50 well regions, resulting in about 625 total regions.

In an exemplary embodiment, the classification module 302 may be configured to classify one or more wells of an array as to whether the well is empty or contains an analyte or substrate associated with an analyte by flowing a known pH buffer at a different pH than a wash buffer onto the wells. If the diffusion rate in the well is slower than an average rate of surrounding neighbors, for example, then the well may be considered to contain a particle. If not, then the well may be identified as empty. Other procedures to establish a baseline pH change over time can include, for example, fitting the signal to exponentials or other models of the expected background signal.

According to an exemplary embodiment, there is provided a method for determining whether a defined space includes an analyte or substrate associated with an analyte, including: (1) changing reagents in a flow chamber from a first reagent that sensors generate in response thereto a first output signal to a second reagent that sensors generate in response thereto a second output signal; and (2) correlating a time delay in the generation of the second output signal in response to the changing of reagents with a presence or absence of an analyte or substrate associated with an analyte. The sensor may be an electrochemical sensor, including a potentiometric sensor, an impedimetric sensor, or an amperometric sensor, for example, or any sensor such that the output signal depends on an interaction between an electrode or other analyte-sensitive surface and a sensor-active reagent whose arrival is delayed by physical or chemical obstructions in a defined space. The sensor-active reagent may be a wash solution at a different pH than the reagent it replaces.

In an exemplary embodiment, the classification module 302 may be further configured to identify and parse sample nucleic acids or fragments based on their type and/or origin. Such identification, which may be useful when using test nucleic acid fragments as a control and/or when pooling and sequencing fragmented samples of nucleic acids from different origin ("multiplexing"), for example, may be based on labeling or tagging of the fragments prior to the sequencing process (e.g., with fluorescent tags). Such identification may be performed using sequencing keys (e.g., a known artificial nucleic acid sequence).

In an exemplary embodiment, a signal processing module or signal processor 303 may be configured to analyze signal information from a defined space or reaction confinement region and an associated sample nucleic acid template. The signal processing module may output a processed signal, which may be considered a raw incorporation signal. The signal processing module 303 may use information and data resulting from the classification module 302 and associated methods, but may also use raw data or raw signals.

In an exemplary embodiment, the signal processing module 303 may be configured to remove noise from raw signal and improve a quality of the signal, which may include an accuracy and a signal-to-noise ratio of the raw signals, for example. Noise, which may be due to various causes including thermal sensitivity of the sensors, electrical potential disturbances in the fluid (such as resistive or thermal noise in the fluids, reference voltage changes due to different fluids contacting the reference electrode), pH changes due to bulk changes in fluids that are passed over the sensor array (referred to herein as "reagent change noise"), stochastic behavior of polymerase function (e.g., incomplete extensions) or failure to completely wash away all dNTPs in a given step (e.g., inappropriate incorporation), for example, may be removed in various ways.

In an exemplary embodiment, the signal processing module 303 may be configured to remove from the data and signals it received some background signal or noise to generate an improved incorporation signal. To minimize computation time, the signal processing module may only process data and signals for defined spaces containing particles and/or having produced a sufficiently strong signal to indicate a nucleotide incorporation event. The background or noise portion of the signal can be present during each flow and can vary over time, across an array of wells, and during an acquisition.

In an exemplary embodiment, the signal processing module 303 may be configured to create an incorporation fitting model, which may have two parts. The first part may include determining the background signal that would have been measured in a given defined space had no nucleotide incorporation event occurred. The second part may include subtracting or otherwise removing (or fitting) the background signal from the raw signal and then examining and analyzing (or fitting) the signal that remains. The result of the incorporation fitting model may be an estimate of incorporation during each nucleotide flow for each well.

In an exemplary embodiment, the signal processing module 303 may be configured to perform or implement one or more of the teachings disclosed in Rearick et al., U.S. patent application Ser. No. 13/339,846, filed Dec. 29, 2011, based on U.S. Prov. Pat. Appl. Nos. 61/428,743, filed Dec. 30, 2010, and 61/429,328, filed Jan. 3, 2011, and in Hubbell, U.S. patent application Ser. No. 13/339,753, filed Dec. 29, 2011, based on U.S. Prov. Pat. Appl. No. 61/428,097, filed Dec. 29, 2010, which are all incorporated by reference herein in their entirety.

In an exemplary embodiment, the signal processing module 303 may receive a MASK file from the classification module 302. The signal processing module 303 may store, transmit, and/or output raw incorporation signals and related information and data in raw WELLS file format, for example. The signal processing module 303 may output a raw incorporation signal per defined space and per flow, for example.

In an exemplary embodiment, a base caller module or base caller 304 may be configured to transform a raw incorporation signal into a base call and compile consecutive base calls associated with a sample nucleic acid template into a read. A base call refers to a particular nucleotide identification (e.g., dATP ("A"), dCTP ("C"), dGTP ("G"), or dTTP ("T")). The base caller module may perform one or more signal normalizations, signal phase and signal droop (e.g., enzyme efficiency loss) estimations, and signal corrections, and it may identify or estimate base calls for each flow for each defined space. The base caller module may share, transmit or output non-incorporation events as well as incorporation events.

In an exemplary embodiment, the base caller module 304 may be configured to normalize a read, which may include initially using raw data and/or signals from the signal processing module. For example, using one or more known expected 1-mer events, which may be identified using sequencing keys, a 1-mer average signal may initially be established and used for normalization. Then, as the base caller module processes each defined space, additional base calls can be accurately determined and additional measurements then can be used to re-normalize the raw signals. Such re-normalization process may improve confidence (e.g., a higher signal-to-noise ratio) of the signal from each defined space.

In an exemplary embodiment, the base caller module 304 may be configured to observe and account for signal droop that in some instances may be attributed to DNA polymerase loss that can occur during a sequencing run. Such DNA polymerase loss may be experienced during nucleotide incorporation events, with values typically in the range of about 0.1% to about 0.2% over the course of a run. By averaging groups of reads in a region together and/or averaging their signals after normalization, an exponential can be fit to the resulting curve, from which the rate of signal loss over time can be extracted to determine an estimate of the DNA polymerase loss during nucleotide incorporation events.

In an exemplary embodiment, the base caller module 304 may be configured to use the signal droop in a signal phase model as a constant for a read. Signal estimates can vary across an array of defined spaces, but signal droop estimates often can be assumed to be fixed for each processed region. The signal phase model can fit parameters, including carry-forward and incomplete extension parameters, which may lead to an estimate of the carry-forward and incomplete extension for each defined space. Polymerase-based carry-forward and incomplete extension phenomena, see, e.g., Margulies et al., NATURE, 437:376-380 (2005), may also be referred to as plus frame shifts and minus frame shifts, see, e.g., Ronaghi et al., GENOME RESEARCH, 11:3-11 (2001), plus-shift effects and minus-shift effects, see Svantesson et al., BIOPHYSICAL CHEMISTRY, 110:129-145 (2004), and extension failures, see U.S. Pat. No. 7,875,440. The resulting values may be averaged over small regions to reduce errors and noise in the fit, which averaging may be done in various ways, including for any given defined space in a manner that uses neighboring defined spaces in small regions while excluding the defined space to which the resulting values may be applied in downstream analysis, as discussed in Davey et al., U.S. Prov. Appl. No. 61/684,221, filed Aug. 17, 2012, which is incorporated by reference herein in its entirety. The output carry-forward and incomplete extension values can be used as inputs to other parts of the base caller module, for example, a solver function.

In an exemplary embodiment, the base caller module 304 may include a solver function that can apply phase and droop estimates to the normalized signals and make predictions of the likely signal measurements for each nucleotide flow for probable nucleotide incorporation events. The solver function can compare the actual measured value to a list of predicted values and the best fit prediction at each nucleotide flow can be used as the base call for that flow. For example, a 0-mer, 1-mer, 2-mer, 3-mer, 4-mer, and higher order nucleotide incorporations can be predicted at each nucleotide flow. The solver function can continue such processing over the entire read. At the end of one pass, a good estimate of all base calls for that read can be made. The solver function then can iterate over the read again, applying the same phase and droop estimates at each nucleotide flow, to refine the base calls.

In an exemplary embodiment, the base caller module 304 may be configured to perform or implement one or more of the teachings disclosed in Davey et al., U.S. patent application Ser. No. 13/283,320, filed Oct. 27, 2011, based on U.S. Prov. Pat. Appl. No. 61/407,377, filed on Oct. 27, 2010, and in Davey et al., U.S. Prov. Appl. No. 61/684,221, filed Aug. 17, 2012, which are all incorporated by reference herein in their entirety.

In an exemplary embodiment, the solver may be configured as a software tool or application with functionality to efficiently solve or determine, from a set of possible or candidate sequences of bases, which sequence is in some sense most consistent with some observed data. Possible or candidate sequences may be evaluated by predicting data that would be expected for such sequences under one or more predictive models and determining how "close" under some distance criterion the predicted data are from the observed data. According to the present disclosure, the solver functionality may be improved through the implementation of modified basecalling methods that are suitable for adaptation on dedicated hardware processors. Various embodiments of the architecture and processing of sample sequence signal data will be described in greater detail hereinbelow.

A general method for basecall identification is provided below, this method is further described in a modified and adapted form capable of implementation in an improved and optimized manner in connection with the components of the basecall processors of the present disclosure. According to the generalized methods for basecall analysis, one may let Y represent observed or measured data (e.g., a vector of values such as an observed or measured ionogram or flowgram, for example, or other sequencing values), let X represent predicted data (e.g., a vector of values such as a predicted ionogram or flowgram), let A represent a set of possible or candidate nucleic acid or base sequences (e.g., the set comprising the possible sequences of A, C, G, and T; the set comprising the possible sequences of A, C, G, and T that have at most a certain length; or any other subset of candidate sequences), and let P represent a set of parameters used by the one or more predictive models (e.g., parameters for the incomplete extension, carry-forward, and droop rates). Then, in an embodiment, the basecall solution may be thought of as a function $f$ that determines for some defined space or reaction confinement regions comprising one or more sample nucleic acids a "best" candidate sequence A* from set A such that $$A^* = f(Y, X(A, P)) = \arg\min_{A,P} D(Y - X(A, P)),$$

where $$\arg\min_{x,y} f(x, y)$$

$f(x, y)$ generally denotes the value (or values) of x and y that would generally minimize the function $f(x,y)$ and where $D(y-x)$ denotes some function of the "distance" between y and x (e.g., a sum of squared distances or any other measure of a distance between vectors, for example).

Such a basecall solution may in principle consider the possible combinations of sequences in set A and values for the parameters in set P to identify an optimal combination of a sequence and parameter values. Of course, such an exhaustive search may be computationally expensive and potentially very time consuming. In practice the search may advantageously be limited to a subset of sequences and subset of candidate values for the parameters. In an embodiment, the search may be facilitated by performing parameter estimation separately from the optimization, dividing the process into two phases. For example, in a first step, the parameters may be estimated. And in a second step, the parameter estimates may be treated as fixed and supplied as inputs to the solver problem, which could then be reformulated as $$A^* = f(Y, X, A, P) = \arg\min_A D(Y - X(A \mid P)),$$

where X (A|P) denotes X as a function of A given some fixed parameters P.

In an exemplary embodiment, if P included three parameters (e.g., incomplete extension, carry-forward, and droop rates represented as IER, CFR, and DR, respectively), then an optimal sequence A* may be found as follows: First, estimates of IER, CFR, and DR may be obtained using any suitable method, including as disclosed in Davey et al., U.S. patent application Ser. No. 13/283,320, filed Oct. 27, 2011, based on U.S. Prov. Pat. Appl. No. 61/407,377, filed on Oct. 27, 2010, and in Davey et al., U.S. Prov. Appl. No. 61/684,221, filed Aug. 17, 2012, which are all incorporated by reference herein in their entirety. Second, A* may be found by solving $$A^* = \arg\min_A D(Y - X(A \mid IER, CFR, DR)),$$

where X (A|P) denotes X as a function of A given some fixed parameters P (e.g., IER, CFR, and DR in this example). Any suitable optimization method may be used to solve this problem. Also, such an approach does not require any particular type or choice of parameters and/or models using such parameters, although better parameters/models may improve accuracy and performance.

In various embodiments, the sequence identification approaches of the present disclosure may go beyond "base-by-base" base calling, and extend to "whole-sequence" or "whole-read" calling (or at least "whole-fragment" calling). That is, the output of a basecall solution as described herein may be a particular sequence that was collectively considered/called, rather than merely a sequence of individual bases that were considered/called one by one and then joined together to form a sequence. As a result, although the predictive modeling may include some incremental base-by-base aspects, for example, it may sometimes be the case that a particular base (e.g., the second) may be deemed to be a T (in the case of a hypothetical output of the solver yielding sequence "ATTGC . . . ") even though one might have made a different base call had one not considered how consistent the predicted data for the entire candidate sequence may be with measured or observed data.

Figure 4:
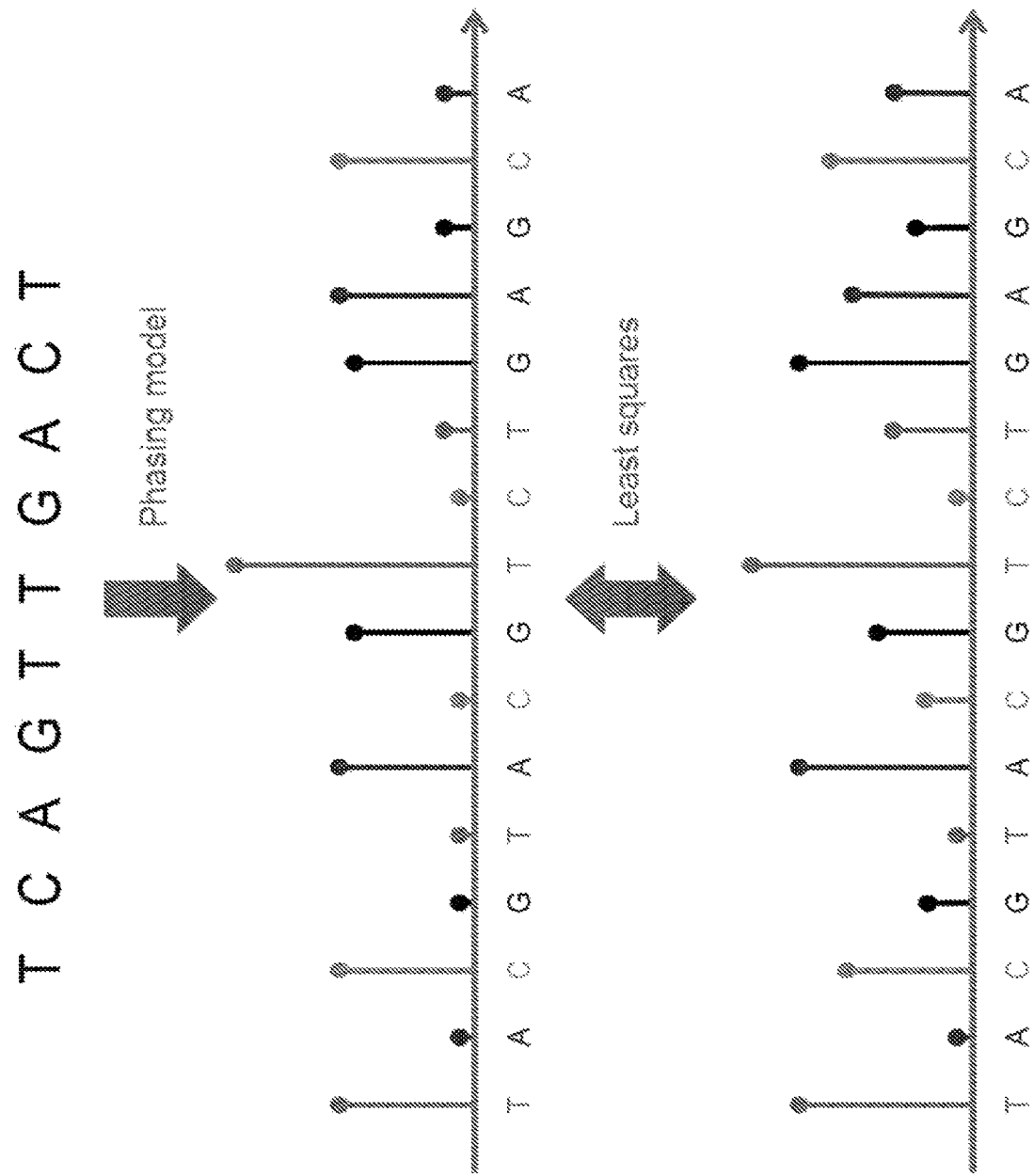
FIG. 4 illustrates an exemplary approach for making base calls in presence of effects capable of causing sequencing errors.

FIG. 4 illustrates conceptually an approach for making base calls in presence of effects capable of causing sequencing errors (such as, e.g., phasing effects), according to an exemplary embodiment. It illustrates schematically the concept of finding as solution a sequence of bases (e.g., T, C, A, G, T, T, G, A, C, and T) for which a predicted set of values (shown in the top graph as, e.g., a predicted ionogram) calculated under a phasing model, for example, is most or closely similar to some hypothetical measured set of values (shown in the bottom graph as, e.g., an observed ionogram) under a least squares framework, for example. Such an approach is tolerant to phasing errors or effects, in the sense that rather than actually removing or correcting such phasing errors or effects from data to subsequently make base calls, the approach can yield base calls that in some way best reflect or take into account such phasing errors or effects. The solution may be found by searching or traversing possible sequences in various ways. For example, the search may be structured as a tree.

Figure 5:
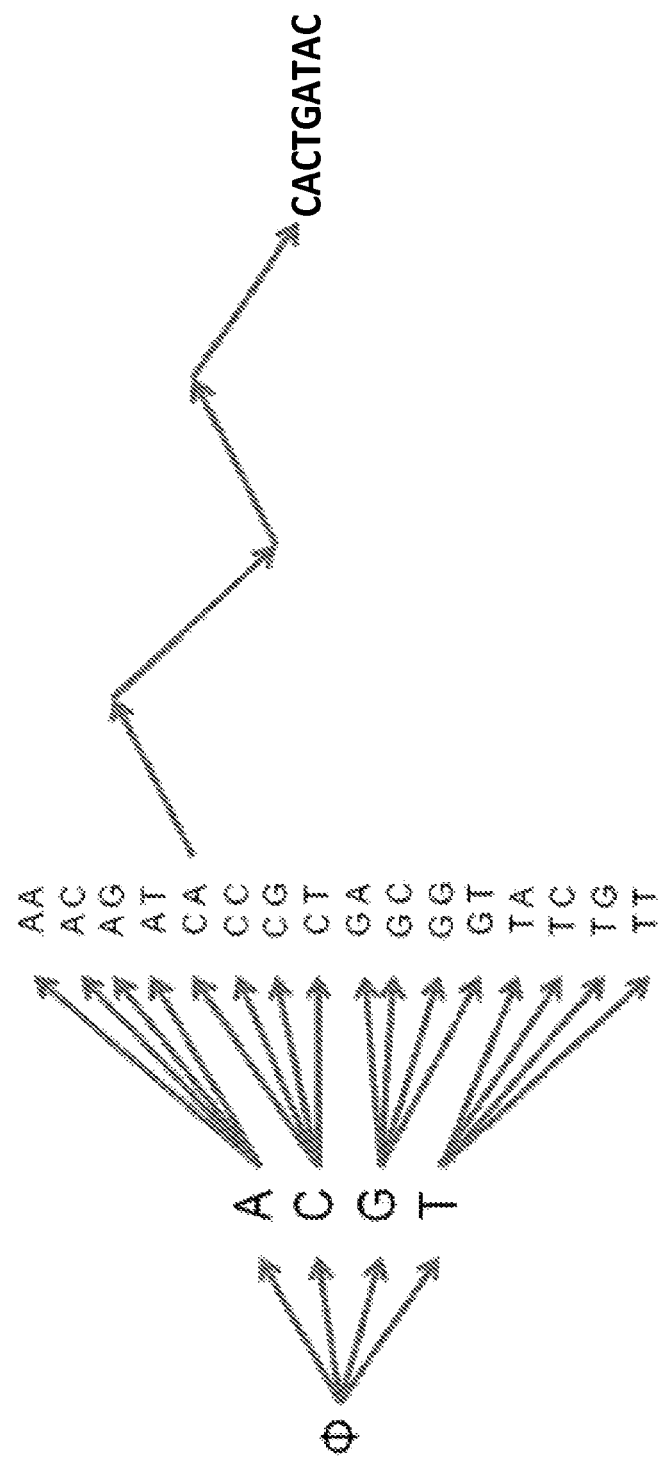
FIG. 5 illustrates a solver for making base calls according to an exemplary embodiment.

FIG. 5 illustrates a solver for making base calls according to an exemplary embodiment. The solver may, for example, be a tree-based solver that determines a sequence of bases that are in some sense most or very consistent with measured data. For example, the solver may determine a sequence of bases (among some or all possible sequences having at most some given maximal length) for which predicted values that would be expected—under one or more models of underlying phenomena and related parameters if such a sequence were subjected to a given ordering of nucleotide flows—are in some sense most similar to measured values for templates actually subjected to the given ordering of nucleotide flows.

The generation of such a data structure may be incremental (e.g., one base at a time, or some number of bases at a time). For example, paths and predicted values may be generated for some partial sequence of length 4 (say, A, G, T, and C) to determine the next base (say, A) leading to a partial sequence of length 5 (say, A, G, T, C, and A) along the corresponding path, and so on. The partial sequences may be organized together, for example, to form a tree, and a "best" sequence may then be represented as a path through the data structure that identifies or leads to a best-fitting sequence under some appropriate metric. In other words, the solver may find the "correct sequence" (e.g., the actual physical base sequence to be determined) by looking at some or all possible sequences (or corresponding paths) having a length up to some selected or maximal length threshold, and determining which one is the "best-fitting sequence" (e.g., the sequence leading to predicted measurements that most closely fit with observed measurements). In an exemplary embodiment, the best-fitting sequence may be the sequence for which a sum of squared distance between an observed ionogram and a predicted ionogram is reduced or minimal.

It should be noted that although such a best-fitting sequence may correspond to or closely match the correct sequence, it is not necessarily the correct sequence both because one or more models used to generate the predicted ionogram may not necessarily reflect all underlying physical phenomena exactly, and because noise in measurements may sometimes cause an incorrect sequence to be a better fit to the observed data purely by chance. In addition, the best-fitting sequence may not always be the optimal solution under the models due to possible overfitting associated with a mismatch between the models and the data.

In such a structured approach, it is in principle possible to consider every possible sequence path or traversal (assuming some given maximal sequence length). However, such an exhaustive approach can be computationally time-consuming depending on complexity. Also, a large number of partial paths may not lead to the best-fitting or optimal sequence when extended and would thus be unnecessarily considered in an exhaustive approach. In an exemplary embodiment, with the use of appropriate metrics, a more efficient search considering some subset of the possible sequence paths may be performed. For example, a solver may examine partial sequence paths, eliminate some from further consideration, and then further examine more promising or informative ones. In an exemplary embodiment, the process of generating partial paths and associated predicted values may be incremental (e.g., one base at a time, or a predetermined numbers of bases at a time).

Figure 6:
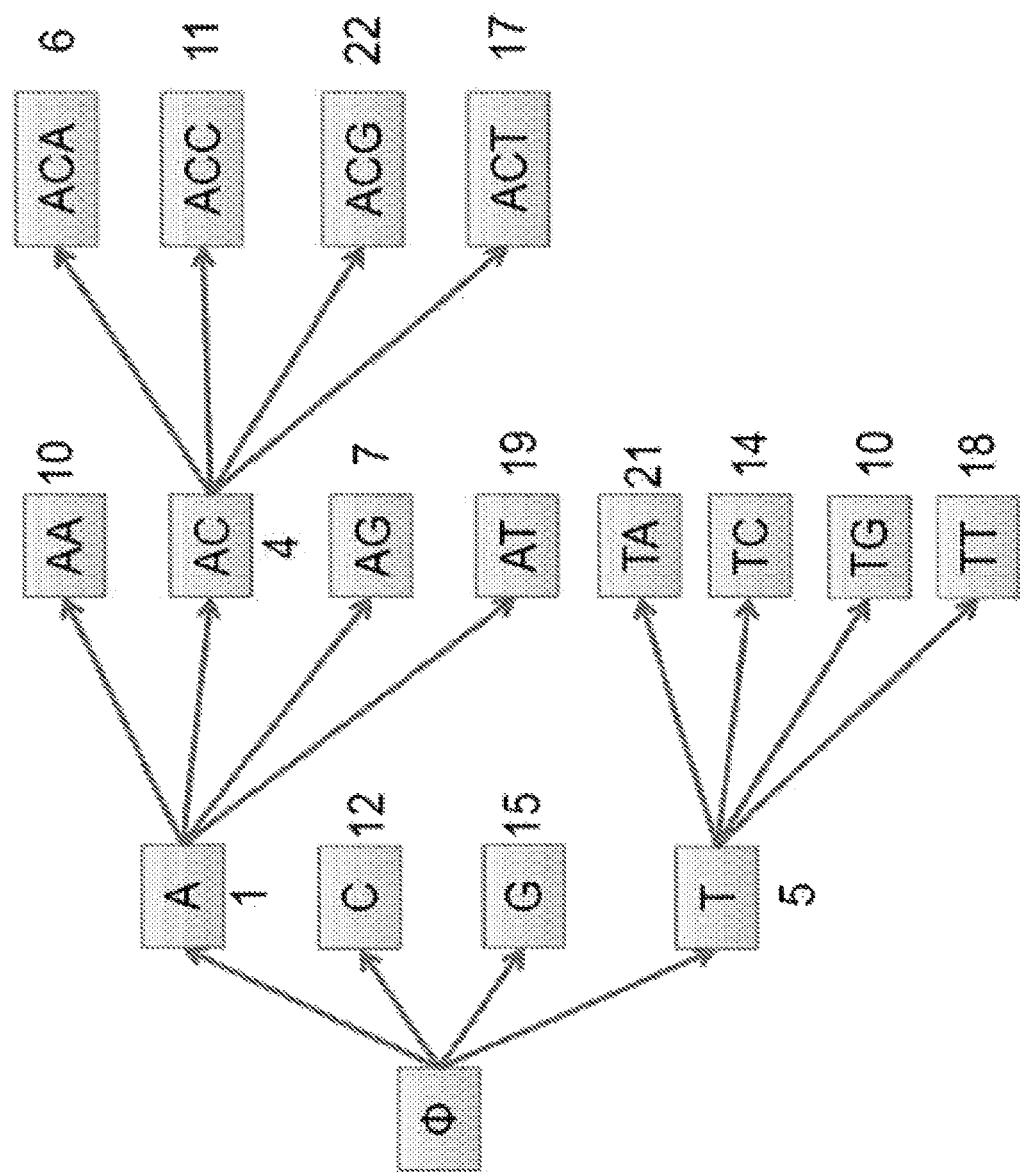
FIG. 6 illustrates a data structure with stepwise progression through partial sequence paths in a solver for making base calls according to an exemplary embodiment.

FIG. 6 illustrates a data structure with stepwise progression through partial sequence paths in a solver for making base calls according to an exemplary embodiment. At the root of the data structure, illustrated in the single box in the first column, there is no base and an exemplary path metric may be assigned a value of zero. There are then four possible 1-nucleotide extensions (A, C, G, and T), which are illustrated in the boxes in the second column. The exemplary path metric has a value of 1 and 5 for nucleotides A and T, respectively, and a value of 12 and 15 for nucleotides C and G, respectively. Here, for example, the partial paths with lower metric values corresponding to nucleotides A and T are selected for further analysis and thus placed on the stack, whereas the partial paths with higher metric values corresponding to nucleotides C and G are not selected for future analysis and removed from the stack (of course, alternative metrics could be devised in which larger values are preferable). There are then four possible 1-nucleotide extensions (A, C, G, and T) for each of the two remaining partial paths, which are illustrated in the boxes in the third column (AA with value 10, AC with value 4, AG with value 7, AT with value 19, TA with value 21, TC with value 14, TG with value 10, and TT with value 18). At this stage, the partial path corresponding to AC has the lowest metric value and is selected for further analysis. There are then four possible 1-nucleotide extensions (A, C, G, and T) for that partial path, which are illustrated in the boxes in the fourth column (ACA with value 6, ACC with value 11, ACG with value 22, and ACT with value 17). This process could continue further to select additional bases along the ACA partial path, which has the lowest metric value at this point. Various criteria could be devised to determine how many paths to preserve at any given stage, which may be based on empirical observations or other rules.

Figure 7:
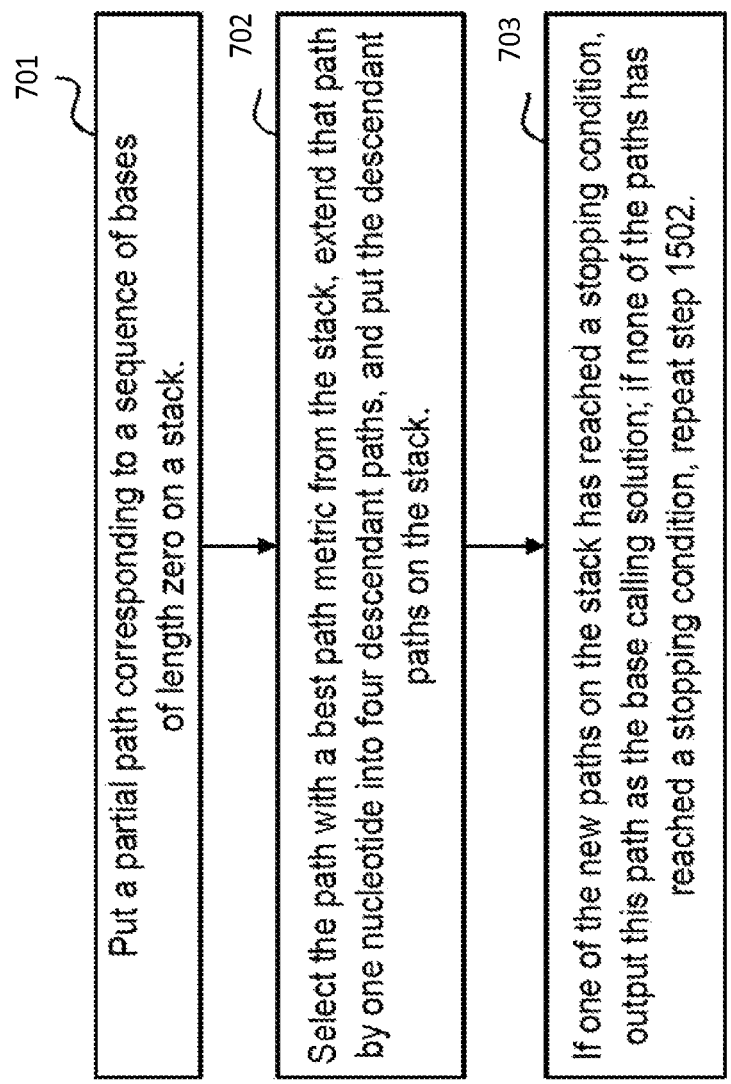
FIG. 7 illustrates a method for stepwise progression through partial sequence paths in a solver for making base calls according to an exemplary embodiment.

FIG. 7 illustrates a method for stepwise progression through partial sequence paths in a solver for making base calls according to an exemplary embodiment. In step 701, a server or other computing means or resource puts a partial path corresponding to a sequence of bases of length zero on a stack. In step 702, a server or other computing means or resource selects the path with a best path metric from the stack, extends that path by one nucleotide into four descendant paths, and puts the descendant paths on the stack. In step 703, a server or other computing means or resource determines if one of the new paths on the stack has reached a stopping condition and, if one has, outputs this path as the base calling solution; if none of the paths has reached a stopping condition, step 702 is repeated.

The performance of such structured approaches may depend on making an appropriate selection of one or more path metric(s). Among full length sequences, a best or optimal fitting sequence, or sequence having a desired fit, may be the one having the lowest or smallest path metric (of course, alternative metrics could be devised in which larger values are preferable). For partial sequences, the path metric may be nondecreasing. It should be noted, however, that the length of the best fitting sequence need not be known a priori. Subject to the level of accuracy of underlying models of sequencing phenomena, path metrics may provide a mechanism in the context of the structured search to identify the best fitting sequence and thus make base calls in a manner that may be more accurate and/or efficient.

Because of phasing effects, individual pieces of observed or measured data (e.g., ionogram values) may be causally affected by multiple nucleotides. As a result, when calling bases (or homopolymers) one-by-one (sequentially), one may have to assume that some of the bases are yet undecided, and that their contribution to the measured data is unknown. Such difficulty in fully leveraging information embedded in measured data can increase risks of missing the global optimum.

Figure 8:
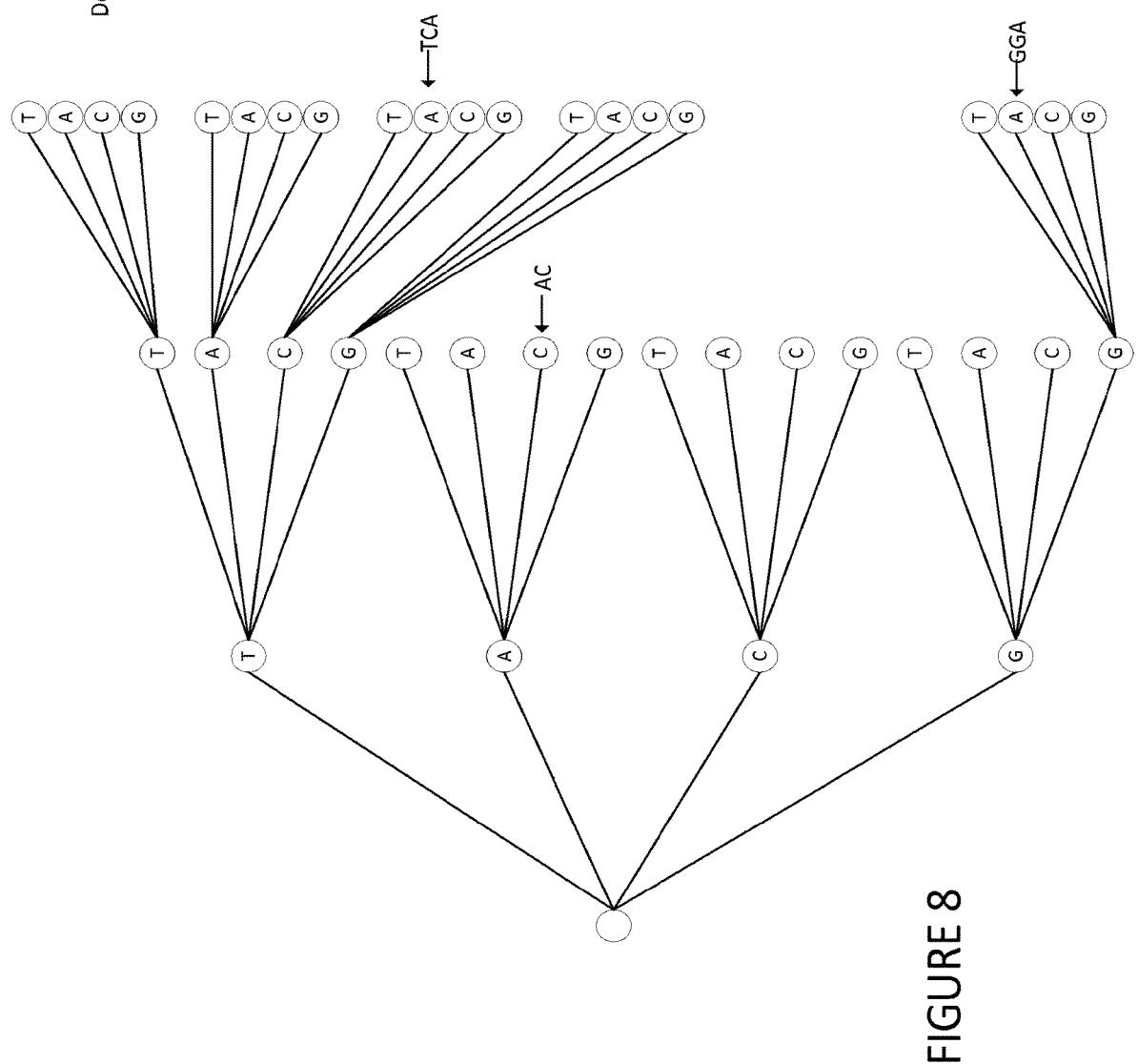
FIG. 8 illustrates a decision point between various exemplary paths in a solver for making base calls according to an exemplary embodiment.

FIG. 8 illustrates a decision point between various exemplary paths in a solver for making base calls according to an exemplary embodiment. There, decision is between paths T-C-A, A-C, and G-G-A. A proper traversal search may overcome local minima and find a better solution. Further, a proper traversal search may end up terminating certain branches early on, and keeping more or less descendants in some branches, in an effort to carefully consider sets of partial sequences that are promising while rapidly removing from consideration sets of partial sequences that are not promising.

Figure 9:
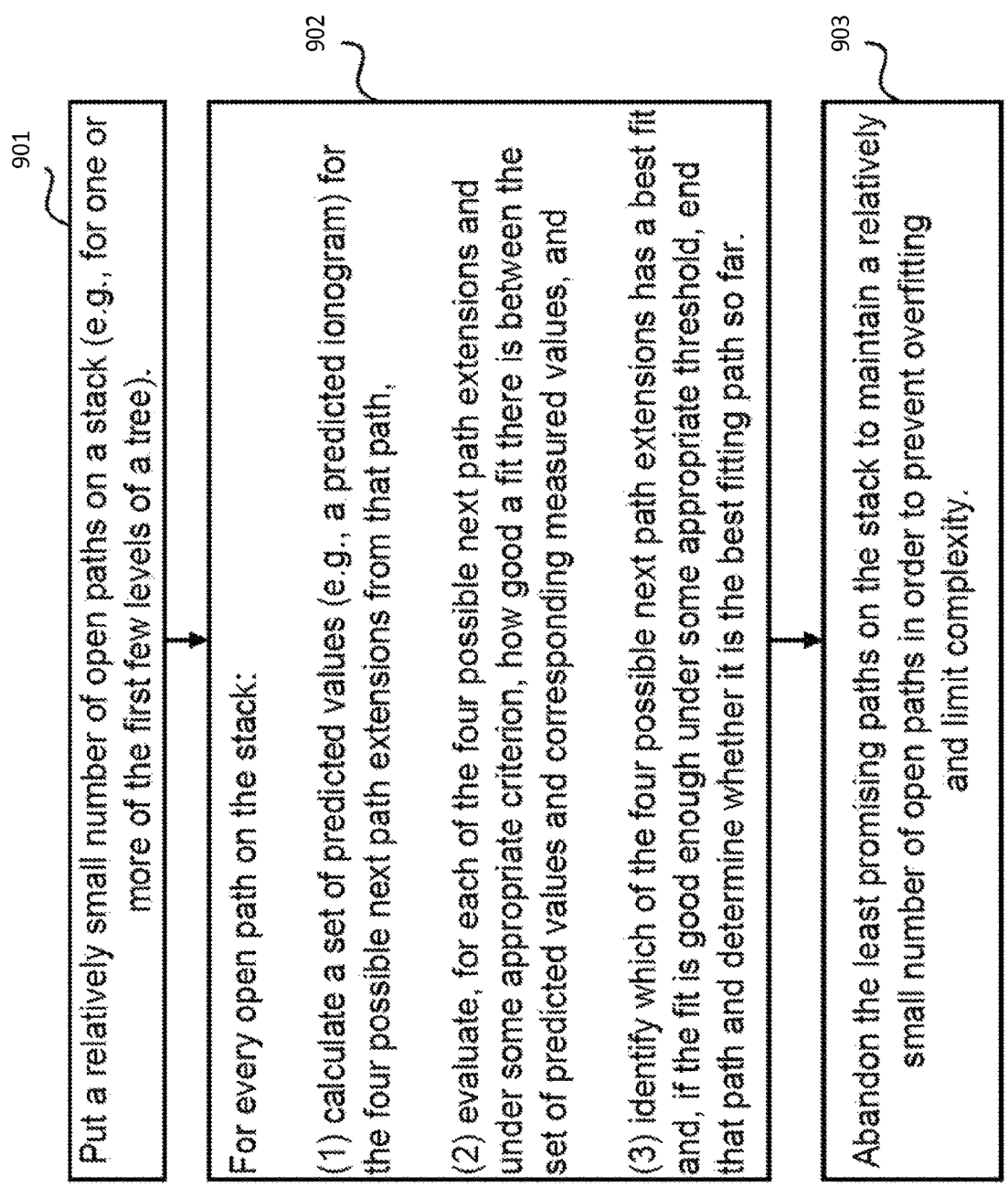
FIG. 9 illustrates a method for stepwise progression through partial sequence paths in a base calling solver according to an exemplary embodiment.

FIG. 9 illustrates a method for stepwise progression through partial sequence paths in a base calling solver according to an exemplary embodiment. In step 901, a server or other computing means or resource puts a relatively small number of open paths on a stack (e.g., for one or more of the first few levels of a tree or other data structure) to help prevent overfitting and limit complexity. In step 902, for every open path on the stack, a server or other computing means or resource calculates a set of predicted values (e.g., a predicted ionogram) for the four possible next path extensions from that path; evaluates, for each of the four possible next path extensions and under some appropriate criterion, how good a fit there is between the set of predicted values and corresponding measured values; and identifies which of the four possible next path extensions has a best fit and, if the fit is good enough under some appropriate threshold, ends that path and determines whether it is the best fitting path so far. In step 903, a server or other computing means or resource terminates or abandons the least promising paths on the stack to maintain a relatively small number of open paths in order to prevent overfitting and limit complexity, which may include terminating or abandoning paths that are too far behind the longest one under some appropriate criterion and, in some cases when comparing paths of different length, terminating or abandoning paths having a path metric with a steepest slope.

In an exemplary embodiment, a base caller may be configured to calculate several metrics for each path. The metrics may be used alone or in various combinations to directly and/or indirectly evaluate the paths. The metrics may include a path metric (e.g., a metric that drives the selection of the next path on the stack to expand), a greedy decision metric (e.g., a local fit metric calculated for four descendants of a just extended path, which may be used in one or more absolute pruning rules), a per-flow metric (e.g., an auxiliary path metric used by a stack size limiting rule), a scaled residual (e.g., another local fit metric that may be used in one or more absolute pruning rules), and a total residual (e.g., a complementary measure to the path metric, which may be used in one or more absolute pruning rules and which may be such that a lowest total residual among visited paths constitutes a good upper bound for the path metric). In an embodiment, these metrics may be closely aligned to the manner in which a partial predicted ionogram is computed, which may done be according to a temporal phasing model as disclosed in Davey et al., U.S. patent application Ser. No. 13/283,320, filed Oct. 27, 2011, based on U.S. Prov. Pat. Appl. No. 61/407,377, filed on Oct. 27, 2010, which are both incorporated by reference herein in their entirety.

To further illustrate such metrics for some read pertaining to some defined space comprising sample nucleic acids subjected to a series of nucleotide flows, let L denote a number of nucleotide flows; let E denote an observed or measured intensity value representative of one or more nucleotide incorporation(s) (or lack thereof) for the samples in response to the ith nucleotide flow; let $Y=(Y_1, Y_2, \ldots, Y_L)$ denote an observed or measured ionogram or flowgram or other sequencing data (e.g., a vector comprising observed or measured intensity values such as, e.g., voltages or signals, responsive to the various nucleotide flows), and let $X=(X_1, X_2, \ldots, X_L)$ denote a predicted ionogram or flowgram or other sequencing data for the path or partial sequence under consideration (e.g., a vector comprising predicted intensity values that would be expected in response to the various flows under one or more models of underlying physical sequencing phenomena). In addition, let (a, b) denote an active window within the nucleotide flows (where a and b respectively denote the earliest and the latest flow during which the last nucleotide in the partial sequence under consideration was incorporated by a substantial subpopulation of the polymerase molecules) and let f denote an "in-phase flow" (e.g., an index for the flow at which the last base would have been incorporated in the absence of any phasing errors or effects).

In an embodiment, a path metric may be a sum of (i) a sum of squared residuals before an active window and (ii) a sum of squared residuals for negative residuals within the active window. For example, such a path metrics may be expressed as Equation 1.1.

$$\text{PathMetric} = \sum_{i=1}^{a-1} (Y_i - X_i)^2 + \sum_{i=a}^{b} \begin{cases} 0 & \text{if } (Y_i - X_i) > 0 \\ (Y_i - X_i)^2 & \text{if } (Y_i - X_i) < 0 \end{cases} \quad \text{Eqn. 1.1}$$

A path metric may also be expressed as Equation 1.2, where $\delta$ and $\varepsilon$ are real numbers, which may differ from zero.

$$\text{PathMetric} = \sum_{i=1}^{a-1} (Y_i - X_i)^2 + \sum_{i=a}^{b} \begin{cases} \delta & \text{if } (Y_i - X_i) > \varepsilon \\ (Y_i - X_i)^2 & \text{if } (Y_i - X_i) < \varepsilon \end{cases} \quad \text{Eqn. 1.2}$$

In an embodiment, a greedy decision metric may be a sum of (i) a product of an empirical constant and a sum of squared residuals for negative residuals within an active window and (ii) a sum of squared residuals for positive residuals within the active window but only before an in-phase flow. For example, such a greedy metrics may be expressed as Equation 2.1, where $\alpha$ is an empirical constant.

$$\text{GreedyMetric} = \alpha \sum_{i=a}^{b} \begin{cases} 0 & \text{if } (Y_i - X_i) > 0 \\ (Y_i - X_i)^2 & \text{if } (Y_i - X_i) < 0 \end{cases} + \quad \text{Eqn. 2.1}$$

-continued $$\sum_{i=a}^{f-1} \begin{cases} (Y_i - X_i)^2 & \text{if } (Y_i - X_i) > 0 \\ 0 & \text{if } (Y_i - X_i) < 0 \end{cases}$$

A greedy decision metric may also be expressed as Equation 2.2, where $\beta$, $\gamma$, $\delta$, and $\varepsilon$ are real numbers, which may differ from zero.

$$\text{GreedyMetric} = \alpha \sum_{i=a}^{b} \begin{cases} \beta & \text{if } (Y_i - X_i) > \gamma \\ (Y_i - X_i)^2 & \text{if } (Y_i - X_i) < \gamma \end{cases} + \quad \text{Eqn. 2.2}$$

$$\sum_{i=a}^{f-1} \begin{cases} (Y_i - X_i)^2 & \text{if } (Y_i - X_i) > \varepsilon \\ \delta & \text{if } (Y_i - X_i) < \varepsilon \end{cases}$$

In an embodiment, a per-flow metric may be a weighted sum of (i) a path metric as described above and (ii) a greedy decision metric as described above. For example, the per-flow metric may be expressed as Equation 3.1, where A may be substantially equal 1/f to and B may be substantially equal to 0.5/f, where f denotes the in-phase flow.

$$\text{PerFlowMetric} = A(\text{PathMetric}) + B(\text{GreedyMetric}). \quad \text{Eqn 3.1}$$

In an embodiment, a scaled residual may be a ratio of (i) a difference between an observed or measured value for a current path at a current in-phase flow and a predicted value from a parent path at the current in-phase flow and (ii) a difference between a predicted value of the current path at the current in-phase flow and a predicted value from the parent path at the current in-phase flow. For example, a scaled residual may be expressed as Equation 3.2.

$$\text{ScaleResidual} = \frac{Y_f - Z_f}{X_f - Z_f}. \quad \text{Eqn. 3.2}$$

In an embodiment, a total residual may be a sum of squared residuals over all nucleotide flows. For example, the total residual may be expressed as Equation 4.1.

$$\text{TotalResidual} = \sum_{i=1}^{L} (Y_i - X_i)^2. \quad \text{Eqn. 4.1}$$

In various embodiments, some or all of the foregoing metrics may be used to allow a more efficient search through and consideration of possible sequences of bases. In an exemplary embodiment, some or all of the foregoing metrics may be used to perform pruning, which may include removing selected paths from the stack to minimize and/or ameliorate possible model overfitting considerations while improving speed. This may obviate the need to spend computational resources considering paths that likely do not lead to the correct sequence, and reduce risks of reporting such likely erroneous paths as final solution. However, pruning may also have downsides. For example, a path removed through pruning may actually lead to the correct sequence. In an exemplary embodiment, to maximize the benefits of pruning while minimizing potential downsides, there is provided a set of rules that are sensitive (e.g., having a low likelihood of removing paths leading to the correct sequence) and specific (e.g., achieving removal of a large number of other paths).

Various rules may be used for pruning, including "absolute" pruning rules and "relative" pruning rules. Absolute pruning rules include rules adapted to decide whether a path is to be removed without any dependency on other paths on the stack. Such absolute rules act on new paths created in an extension step, and usually act quickly. Relative pruning rules include rules adapted to decide whether a path is to be removed depending on other paths on the stack. Such relative rules may entail periodic scanning of the stack for paths that match the rule at a given point in time (even though in some cases the same paths may not previously have matched the rule).

As will be described in detail below, the present methods are distinguished from other basecall determination methods such as the "treephaser" methods described in Sikora et al., U.S. Patent Application Publication Nos. 2013/0060482 and 2013/0090860 by a number of beneficial enhancements giving rise to improved performance. For example, the basecall methods of the present disclosure are capable of de-phasing a complete "top candidate" or best selection path to its terminal state and retaining a finite list of "good candidates" basecalls along that path to be subsequently evaluated. Top candidate paths typically do not terminate early unless an associated quality metric falls below a threshold level or in comparison to other identified candidate paths. In various embodiments, where another candidate path appears as better quality (e.g. after being de-phased to its end state), the previous top candidate path may be replaced by the new top candidate path.

The present methods avoid potential computational inefficiencies of other basecalling methods for example where deep basecalling paths are evaluated at significant CPU cost that end up being discarded. Additionally, the present methods are able to deterministically identify preferred basecall paths allowing for buffer synchronization in contrast to other methods where the time to find the preferred path is not deterministic.

While other approaches may fail to identify the correct basecall path as a result of quality metrics falling below other candidate paths at the point of branching the present methods desirably avoid paths lost in this manner.

According to the present methods, parallel predictive basecall processing (e.g. parallel "Treephaser") may extend each candidate path simultaneously in parallel, so the quality metrics being compared are for the same sequence length. Extension of each path together further provides for the ability to share common processing functions, reducing computational effort required where significant calculations that are similar for any extended base sequence.

In various embodiments, the parallel basecalling methods described herein have an algorithmic time complexity of $O(n^2)$ compared to other methods having a time complexity of $pO(n^3)$; where "p" is the average number of paths that need exploring. In various embodiments, de-phasing window length is a tuning parameter that can have an impact on the quality of the resulting sequence and the computational effort required. Previous methods implemented a median calculation (having $O(n^2)$ complexity) several times per window resulting in an additional order of complexity in the computational methods. In various embodiments, the parallel Treephaser methods described herein apply linear median approximation approaches, reducing an order of complexity, while enabling highly efficient parallel implementation that uses a single pass of the data.

In various embodiments, the offset and gain ramping approaches described herein with respect to windowed offset and gain normalization differs from other methods. In existing approaches, a first half-window segment uses a fixed normalization value that is generally equal to the median of the window; values are then ramped from mid-window to mid-window. According to the present methods, parallel Treephaser applies a ramp to the first half-window segment, starting the gain at 1.0 and the offset at 0.0. This approach is practical as the data is "pre-normalized" such that the first few nucleotide flows to be considered have gain and offset errors removed. As a result, fewer early flow base call errors are encountered by applying the present methods.

Finally, existing basecalling methods may re-normalize the sequencing data (using a "windowed offset and gain normalization" algorithm) once every window number of flows to reduce CPU load. Normalizing the data removes gain and offset errors that impede accurate basecalling. Errors tend to accumulate towards the end of the normalization window (as is evident in the saw-tooth pattern in per-flow quality metrics). According to the present disclosure, the methods for parallel Treephasing may be configured to re-normalize with each iteration, improving base calling accuracy. In the present methods, parallel implementation provides for little or no penalty for re-normalizing every iteration as it may be integrated into the analysis pipeline.

Figure 10:
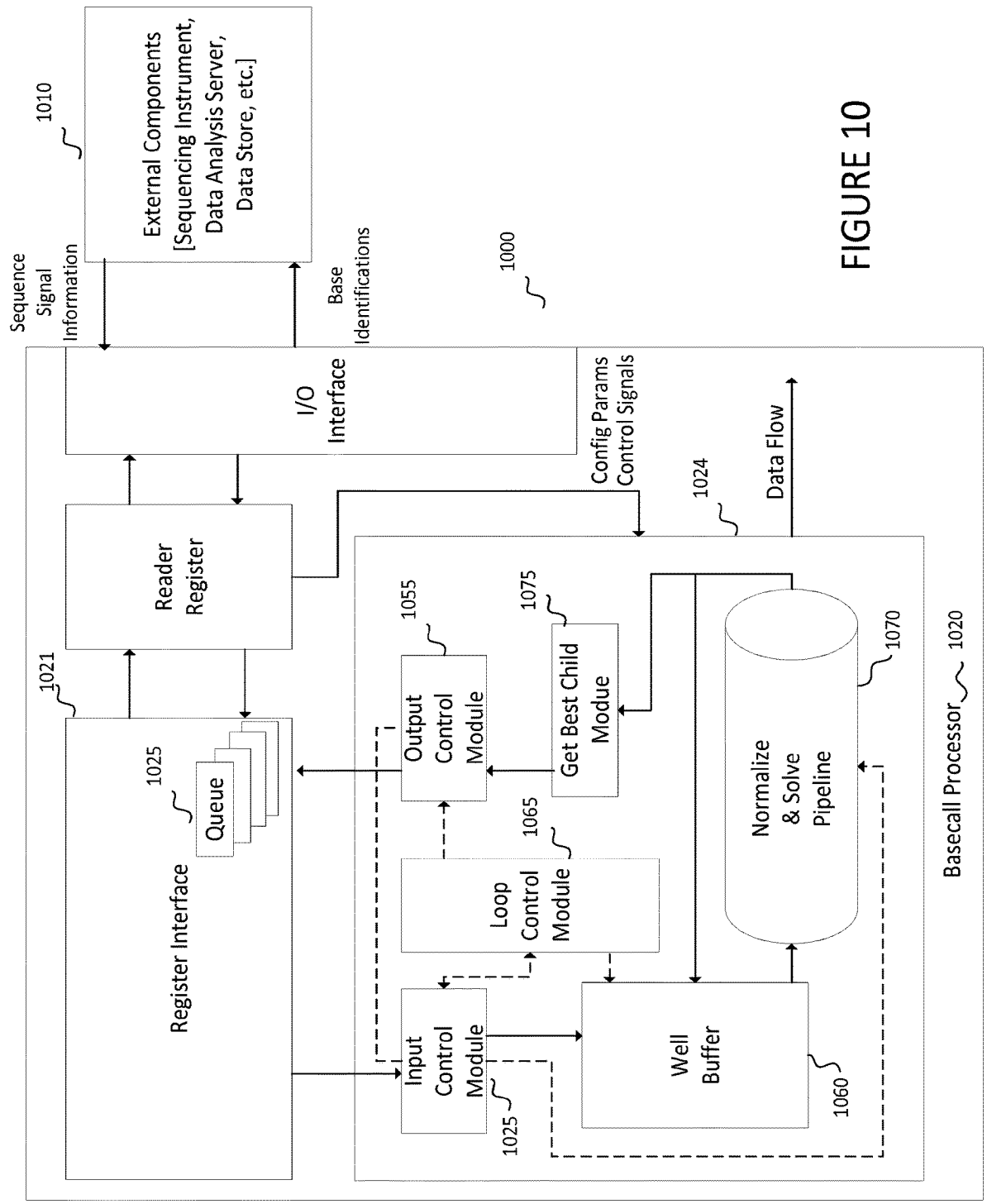
FIG. 10 illustrates an embodiment of hardware components and functionality associated with an exemplary basecall processor architecture for sequence data analysis according to the present disclosure.

FIG. 10 illustrates an exemplary basecall processor architecture 1000 for sequence data analysis according to the present disclosure. In various embodiments, a basecall processor 1020 may comprise one or more dedicated hardware components configured to receive sequencing signal information generated by the sequencing system or instrument 1010. The hardware components may further comprise a programmable FPGA or GPU board configured to process the sequencing signal information according to the methods described herein. In various exemplary embodiments, the FPGA board may comprise a commercially available programmable product such as the Stratix V FPGA (Altera Corporation, San Jose, California). Information regarding field programmable gate array ("FPGA") technology and/or graphics processing unit ("GPU") technology may be obtained from the following documents which are incorporated by reference herein in their entirety: Woods, R., et al., *FPGA-based Implementation of Signal Processing Systems*, John Wiley & Sons (2008); Gallagher, S., *Mapping DSP Algorithms Into FPGAs*, Xilinx, Inc., available at http://www.ieeeli/pdf/viewgraphs/mapping_dsp_algorithms_into_fpgas.pdf; and Bartholomä, R., et al., *Implementing Signal Processing Algorithms on FPGAs*, University of Applied Sciences Pforzheim, Germany, available at http://citeseerx.ist.psu.edu/viewdoc/download?doi=10.1.1.130.8731&rep=rep1&type=pdf.

In various embodiments, the basecall processor 1020 is configured to receive signal information representative of data obtained from the sequencing platform or instrument 1010. The basecall processor 1020 may be embedded or associated directly with the sequencing instrument 1010 or reside in a separate computing instrument or platform configured to receive sequence signal information transmitted directly from the sequencing instrument 1010 or process the sequencing signal information stored in a file or other data structure.

In various embodiments, the basecall processor 1020 is configured to independently or semi-independently process the sequence signal information directly thereby freeing up computing resources associated with other sequence analysis systems or subsystems such that they are not encumbered or substantially slowed down during the processing of the sequence signal information.

According to certain embodiments, a register interface 1021 of the basecall processor 200 coordinates the receiving of sequence signal information from the sequencing instrument or other data store 1010 as described above. In various embodiments, the register interface 1021 acts as a data intermediary or gatekeeper between components the basecall processor 1020 and the sequencing instrument or other data store by directing the receipt of sequencing signal information in one or more data queues configured to store and prepare sequence signal information for processing by the basecall processor 1020.

The register interface 1021 may further be configured in a direct memory access (DMA) mode where the basecall processor 1020 is configured to interface with other hardware subsystems (e.g. for example on the sequencing instrument or data analysis server 1010) and provide access to system memory or resources independently of a central processing unit (CPU) associated with the hardware subsystems. Configuration of the architecture in this manner desirably reduces consuming or leveraging other compute resources which may be slower and subject to limited availability.

A reader register 1022 communicates with an input/output (I/O) interface 1023 associated with the register interface 1021. In various embodiments, the input/output interface 1023 receives sequence signal information from outside of the basecall processor 1020 through a conventional I/O port such as, for example, a PCI or PCIe data transport interface and may further be configured to manage information reads and writes to the one or more queues 1025 of the register interface 1021.

A basecall processing module 1024 is configured to request and receive the sequence signal information from the register interface queue 1025. The basecall processing module 1024 may further implement the sequence signal analysis methods and logic that resolve sequence signals to identify associated basecalls representative of the nucleotide sequence for a plurality of nucleic acids samples or templates (e.g. sequence or nucleotide "reads").

An input control module 1025 manages data to be processed by the basecall processor 1020 including sequence signal information, configuration parameters, tuning parameters, and other information used by the basecall processor 1020 as will be described in greater detail hereinbelow. In various embodiments, the parameters received and passed by the input control module 1025 are used in the sequence signal resolution methodology implemented in the basecall processor 1020. For example, the basecall processor 1020 may be configured to perform basecalling according to general methods that have been adapted for processing on the basecall processor 1020. Exemplary basecalling methods are described in U.S. patent application Ser. Nos. 13/588,408 and 13/645,058 both entitled "Methods, Systems, and Computer Readable Media for Making Base Calls in Nucleic Acid Sequencing" which are hereby incorporated by reference in their entirety. The basecalling methods include various expected input parameters and information such as the sequencing signal data, information about expected data window lengths, information about expected template read lengths and other information including configuration parameters and control signals.

An output control module 1055 further handles pushing or transmitting processed signal data from the basecall processor 1020 to other external components through the register interface 1021. In various embodiments, the output control module 1055 outputs analysed sequence information including basecalls that have been identified in association with the sequence signal data.

The input control module 1025 and output control module 1055 may be configured to coordinate I/O activities such that the basecall processor 1020 remains primed or loaded with sequence signal data such that the basecall processor 1020 operates with a high degree of efficiency with little or no latency arising from dwell or wait times to receive sequencing data to be processed or transmit processed basecalls from the basecall processor 1020.

In various embodiments, the register interface 1021, input control module 1025, and output control module 1055 are configured to operate substantially independently from other components outside of the basecall processor 1020 including external components 1010. Configuration of the architecture in this manner may desirably permit the basecall processor 1020 to operate using an independent clock and may further facilitate isolation of the components of the base call processor 1020.

The well buffer 1060, loop control module 1065, normalize & solve pipeline 1070, and get best child module 1075 represent functionalities associated with solving for basecalls according to the methods described in further detail below. In various embodiments, the well buffer 1060, receives sequence signal information from the input control module 1025 and putative basecalls from the normalize & solve pipeline 1070. The well buffer 1060 may store current estimations or solutions for identifying or resolving the sequence associated with the sequence signal and supplies the normalize and solve pipeline 1070 with sequencing signal data and putative basecalls to be processed. The get best child module 1075 maintains a copy of the putative or best candidate base call provided by the normalize and solve pipeline 1070. Upon completion of the basecalling analysis for a given round of signal processing, the get best child module may forward the putative basecall to the output control module 1155 for transmission to other components outside of the basecall processor 1020.

Figure 11:
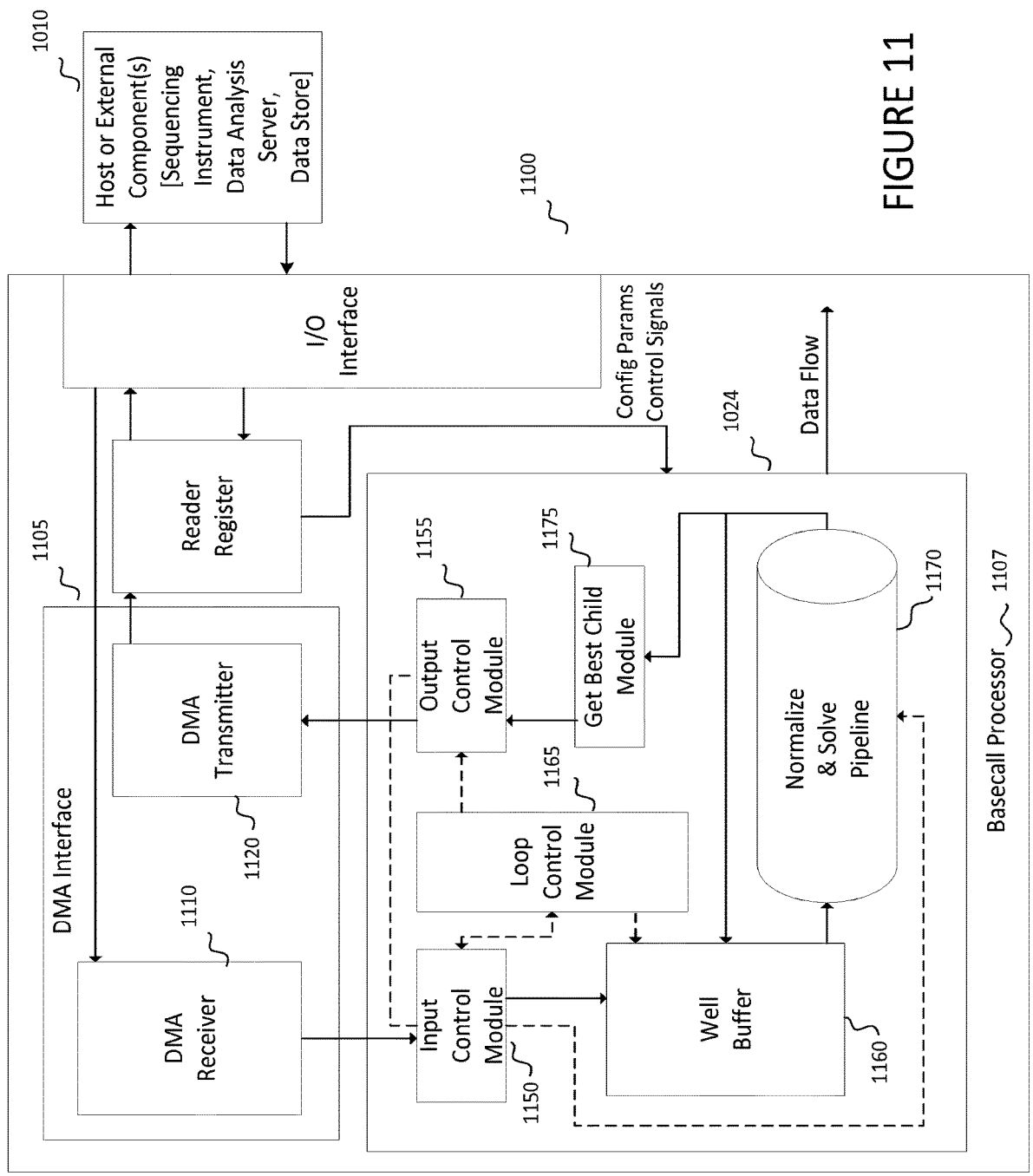
FIG. 11 illustrates another embodiment of hardware components and functionality associated with an exemplary basecall processor architecture for sequence data analysis according to the present disclosure.

FIG. 11 illustrates another embodiment of hardware components and functionality associated with an exemplary basecall processor architecture 1100 for sequence data analysis according to the present disclosure. The previously described register interface 1021 and associated queue(s) 1025 may be replaced with a dedicated direct memory access (DMA) interface 1105 comprising a DMA receiver 1110 and DMA transmitter 1120 interface. In various embodiments, at least a portion of the registers of the register interface 1021 may be retained to maintain various configuration parameters, co-processor controls, and other information. The registers may further receive information that is associated with or ancillary to data packets containing sequence signal information to be processed by the DMA interface 1105. An exemplary DMA packet structure for sequence signal processing is discussed in greater detail below.

In various embodiments, the DMA interface 1105 receives and processes data packets containing sequence signal information associated with sample sequence data to be analysed. In various embodiments, a basecall processor 1107 executes a basecall processing routine information using the data packets provided by the DMA interface. The DMA interface 1105 is configured to supply the basecall processor with sequencing signal data with little or no dwell time desirably reducing the amount of clock cycles required to process the sequence signal data. Over the course of analysis, owing in part to the large amount of discrete samples to be processed and the computational complexity of the analysis, the DMA data transmission efficiency results in substantially reduced analysis times and improved performance as incoming sequence signals are resolved to basecalls.

Such a hardware configuration may further enhance data transfer speeds and throughput between the host/external components and the basecall processor 1107. Enhancements to the I/O capabilities of the basecall processor 1107 are desirable to avoid bottlenecks in receiving sequence signal information or outputting basecall information. In various embodiments, configuring a dedicated DMA interface 1105 as described herein may facilitate real-time results processing of sequence data providing for more immediate access to sequence data results. It will be appreciated that such improvements can be helpful to aid users, clinicians and researchers in arriving at actionable sequencing results or to facilitate further downstream analysis including sequence alignment, mutational/variant analysis, target sequence identification, etc.

According to various embodiments command and control of information flow through the basecall processor 1020 is directed by information contained in data packets passed to the basecall processor 120. Details of an exemplary packet structure will be described in greater detail below. A header contained in the data packet may first be read and the phasing and flow parameters loaded into the basecall processor 1020. A first well may then be read into the well buffer 1060, 1160 as discussed below where processing starts. A subsequent well may then be read from the input DMA receiver 1110 when the first well has completed processing and has started being written to the output DMA transmitter 1120.

A well analysis may be deemed complete when there are no valid outputs from the normalize & solve pipeline 1170. In various embodiments, the output control module 1155 maintains a buffer with the best output (e.g. putative basecall) that has been passed to it since the last time it flushed the buffer. In the case where no valid outputs are received, this may trigger a new flush of the data where the buffer is updated only when there is another iteration with better output (e.g. lower sum of squares) than what is currently stored. In various embodiments, such processing restrictions prevent for example erroneously long homopolymers (e.g. stretches of a singular nucleotide or base sequence such as "AAAAA", "GGGGGGG", "CC", "TTTTTTTTTT" (SEQ ID NO: 1)) from overwriting sequence information that has already completed analysis.

The following description provides an overview of an exemplary packet structure that may be implemented in connection with the basecall processor 1107. In various embodiments, the organization of sequencing signal data and results (both interim and final) within the packet desirably improves the efficiency of analysis relative to conventional methods. While some of the various exemplary embodiments are described as extending the sequencing signal analysis methods described in detail in Davey et al., U.S. Patent Application Publication No. 2012/0109598, and Sikora et al., U.S. Patent Application Publication Nos. 2013/0060482 and 2013/0090860 it will be appreciated that these approaches may be applied to other data analysis systems and technologies.

An exemplary packet structure for containing and transmitting various data corresponding to sample sequence information obtained from a sequencing instrument 100 may be configured in various sizes of bit fields. The data contained in the packets may comprise one or more selected samples to be analyzed. The samples and associated data may further correspond to one or more wells of a sample sequencing array 100. Data transmitted to the basecall processor 1107 according to the methods and hardware components described above may further be analyzed according to modified "tree-phasing" methods.

In various embodiments, data packets may be padded to generally match or conform to the size of a DMA well buffer 1160 (shown in FIG. 11). In various embodiments, a DMA queue associated with the basecall processor 1107 is configured to be 128 bits wide where sections of the packet are 128-bit aligned. Data fields may further be configured as 32-bit aligned to reduce the complexity of packing and to reduce computational load.

An exemplary packet structure is reflected in Table 1 below where the packets may be used to exchange sequence signal information and other data between the basecall processor 1100 and the host or external components 1010. Table 2 provides exemplary register flags that may be used to configure and direct processing in the computational pipeline. Table 3 provides exemplary mappings to convert textual representations of the nucleotide bases into numerical values (for example providing ASCII to uint8 mapping) representative of cyclic flow orderings such as those obtained from the sequencing instrument 10.

TABLE 1

| | bits | | | |
|---|---|---|---|---|
| | 127    96 | 95    64 | 63    32 | 31    0 |
| Idle/Pad | | 0xFFFFFFFFFFFFFFFFFFFFFFFF | | |
| Start-of-frame | | 0x0F1E2D3C4B5A69788796A5B4C3D2E1F0 | | |
| Header | Wells in region (uint32) [1 . . . 2500] | CF parameter (float32) [0.0f..1.0f] | IE parameter (float32) [0.0f . . . 1.0f] | DR parameter (float32) [0.0f . . . 1.0f] |
| | Total num flows (uint32) [1 . . . 2000] | Cyclic num flows (uint32) [1 . . . 2000] | Window size (uint32) [1 . . . 63] | Flags |
| | Zeromer max (float32) [0.300f] | Onemer min (float32) [0.500f] | Onemer max (float32) [4.500f] | DMA packet size in 128b words (uint32) |

TABLE 1-continued

| | bits | | | | | | | |
|---|---|---|---|---|---|---|---|---|
| | 127 | 96 | 95 | 64 | 63 | 32 | 31 | 0 |
| Cyclic Flow Order | CFO[15] (uchar8 × 4) | CFO[12] | CFO[11] (uchar8 × 4) | CFO[8] | CFO[7] (uchar8 × 4) | CFO[4] | CFO[3] (uchar8 × 4) | CFO[0] |
| | CFO[31] (uchar8 × 4) | CFO[28] | CFO[27] (uchar8 × 4) | CFO[24] | CFO[23] (uchar8 × 4) | CFO[20] | CFO[19] (uchar8 × 4) | CFO[16] |
| | . . . | | | | | | | |
| | 0x00 (uchar8 × 4) | 0x00 | 0x00 (uchar8 × 4) | 0x00 | 0x00 (uchar8 × 4) | CFO[n] | CFO[n-1] (uchar8 × 4) | CFO[n-4] |
| Recal Table | B[0][1] (float32) | | A[0][1] (float32) | | B[0][0] (float32) | | A[0][0] (float32) | |
| | B[0][3] (float32) | | A[0][3] (float32) | | B[0][2] (float32) | | A[0][2] (float32) | |
| | . . . | | | | | | | |
| | Pad 0x00000000 (0.0f) | | Pad 0x00000000 (0.0f) | | B[0][tot_flows-1] (float32) | | A[0][tot_flows-1] (float32) | |
| | B[1][1] (float32) | | A[1][1] (float32) | | B[1][0] (float32) | | A[1][0] (float32) | |
| | B[1][3] (float32) | | A[1][3] (float32) | | B[1][2] (float32) | | A[1][2] (float32) | |
| | . . . | | | | | | | |
| | Pad 0x00000000 | | Pad 0x00000000 | | B[hp][tot_flows-1] (float32) | | A[hp][tot_flows-1] (float32) | |
| Raw Well Data | Reserved 0x00000000 | | Reserved 0x00000000 | | Reserved 0x00000000 | | Well ID (uint32) | |
| | Raw[3] (float32) | | Raw[2] (float32) | | Raw[1] (float32) | | Raw[0] (float32) | |
| | . . . | | | | | | | |
| | Pad 0x00000000 (0.0f) | | Pad 0x00000000 (0.0f) | | Raw[tot_flows-1] (float32) | | Raw[tot_flows-2] (float32) | |
| | Reserved 0x00000000 | | Reserved 0x00000000 | | Reserved 0x00000000 | | Well ID (uint32) | |
| | Raw[3] (float32) | | Raw[2] (float32) | | Raw[1] (float32) | | Raw[0] (float32) | |
| | . . . | | | | | | | |
| | Pad 0x00000000 (0.01) | | Pad 0x00000000 (0.0f) | | Raw[tot_flows-1] (float32) | | Raw[tot_flows-2] (float32) | |
| | . . . | | | | | | | |
| Pad DMA Packet | | | | 0xFFFFFFFFFFFFFFFFFFFFFFFF | | | | |
| | | | | . . . | | | | |
| | | | | 0xFFFFFFFFFFFFFFFFFFFFFFFF | | | | |

TABLE 2

| Flag | Description | Default Value | Bits |
|---|---|---|---|
| MaxRecalHP | Number of recalibration table rows. Must be 10 or less, as the FPGA only supports a maximum of 10. Total number of 128-bit words transferred for the Recal Table is ceiling(MaxRecalHP * TotalNumFlows * 0.5). | 10 [1 . . . 10] | 3 . . . 0 |
| RecalEna | Enables recalibration processing when set to 1, disables when set to 0. MaxRecalHP is ignored and no Recal Table is transferred when RecalEna is set to 0. | 0 [0 . . . 1] | 4 |
| Reserved | Reserved for future use | n/a | 29 . . . 5 |
| EnableNormalizer | Enable the normalizer to be used during the base calling process. This flag should always be set to 1 unless the normalizer needs to be bypassed for a specific experiment. Setting this flag to 0 effectively makes the co-processor a straight iterative branching solver. | 1 [0 . . . 1] | 30 |

TABLE 2-continued

| Flag | Description | Default Value | Bits |
|---|---|---|---|
| FlushDMA | Read (flush) the pad words between the end of the last raw well data and the end of the DMA packet when set to 1. Stop reading at the end of the last raw well when set to 0. Setting this flag to 0 allows the next packet to be processed without needing to flush to a DMA buffer boundary. This flag must be set for the last packet. | 1 [0 . . . 1] | 31 |

TABLE 3

| Base | ASCII | Hex | Value |
|---|---|---|---|
| A | 'A' or 'a' | 0 × 41 or 0 × 61 | 0 × 80 |
| C | 'C' or 'c' | 0 × 43 or 0 × 63 | 0 × 81 |
| G | 'G' or 'g' | 0 × 47 or 0 × 67 | 0 × 82 |
| T | 'T' or 't' | 0 × 54 or 0 × 74 | 0 × 83 |

In various embodiments, the most significant bit (MSB) of the cyclic flow order uint8 values may be used to indicate a valid basecall. Pad values can be used and comprise any value for example in the range 0x00 to 0x7F. In the illustrated examples, these pad values are specified as 0x00 for consistency. In some embodiments, selected bits (e.g. for example 6 . . . 2) may be ignored using instead a selected bit (for example, bit 7) as a "valid" flag with bits 1 . . . 0 representing the base or nucleotide identity.

In various embodiments, the base mapping can be efficiently implemented using an approach such as: inline unsigned char MapBaseToFPGA(char base)

```
{
    static unsigned char baseMap[8] = {0x00, 0x80, 0x00, 0x81, 0x83,
    0x00, 0x00, 0x82};
    return baseMap[base & 0x07];
}
```

The cyclic flow order may be zero-padded to conform to a packet boundary such as a 128-bit boundary. A selected flow order may be encoded in the packet structure, for example various flow orders may follow a 32 base cyclic flow ordering. Such a flow ordering may be configured to fit into two 128-bit words. It will be appreciated, however, that the basecall processor can be configured to support other flow orders greater or lesser in number. For example, a 2048 base flow ordering of non-repeating sequences may be configured in this manner.

In various embodiments, recalibration data is transmitted in the packets as pairs of values (for example, a value corresponding to an "A" vector and a value corresponding to a "B" vector). Such information may further be transmitted in ascending order. Each 128-bit word therefore may contain two (A, B) pairs. In instances where the total number of flows is odd, the last (A, B) pair for a given sequence length (e.g. for example a homo-polymer sequence) may be zero-padded so that the next homo-polymer starts at a 128-bit boundary. The total number of (A, B) pairs are configured to be equal to the total number of flows, multiplied by the total number of homo-polymer vectors (MaxRecalHP field in the flags register). For example, a 320 flow run with MaxRecalHP=10 would apply 3200 (A, B) pairs, which is 1600× 128-bit words. In various embodiments, the recalibration table is not transferred if the recalibration enable flag (bit 4 of flags register) is cleared; in this case the basecall processor 1107 may expect the next value to be the start of sequence signal data (e.g. for example raw wells signal data).

In various embodiments, sequence signal data is configured to start at a 128-bit boundary. In many instances, the total number of flows represents a value that is a multiple of four and therefore fits neatly into 128-bit alignment according to the packet structure. Such data configurations are not necessary, however, and instead the end of each well's raw data can be zero padded for example to the next 128-bit boundary. In the exemplary embodiment, bits 127 . . . 32 of the first 128-bit word may be reserved for other uses, such as well-specific parameters or as an additional data block with the lower 32 bits used for the well ID.

The DMA packet size value in the header may be limited to a value no greater than an expected number of samples or wells to be processed. For example, a 26-bit value may be used where the largest theoretical data size is 33,630,341 128-bit words corresponding to a maximum selected number of 64,000 wells with 2000 nucleotide flows, fully defined flow order, and full re-calibration table extending to 10 homo-polymers.

According to various embodiments, a packet structure for containing base-called results capable to be transmitted from the basecall processor 300 back to the host or external components is described below with respect to Table 4. A DMA queue associated with the DMA transmitter 1120 may be configured to 128 bits wide thereby aligned with the aforementioned 128-bit data packets. Data fields may further be configured as 32-bit aligned to further simplify unpacking and aid in reducing computational load. In various embodiments, the length of the packet may not be known ahead of time, however, the number of well result sub-packets will be known. After well results within an analysis region are transmitted, the DMA buffer may be padded to a next frame boundary to help ensure smooth data transfer.

As illustrated in Table 5, a variable size data structure may be used to contain well data comprising basecalls made by the basecall processor 1107. In various embodiments, the well result sub-packets may be configured to contain the called base sequence (basecalls), residuals and normalizer values for a selected well. Well data may be returned in any order and flexible to when the basecall processor 1107 completes processing. In various embodiments, a short sub-packet structure may conform to a 1×128-bit word (header only, sequence length set to zero); and a long sub-packet structure may conform, for example, to 2251×1 128-bit words (header+4000 bases+2000 flows worth of predictions, residuals, gains and offsets according to the example).

TABLE 4

| | bits | | | |
|---|---|---|---|---|
| | 127  96 | 95  64 | 63  32 | 31  0 |
| Start-of-frame | | 0x0F1E2D3C4B5A69788796A5B4C3D2E1F0 | | |
| Header | Reserved 0x00000000 | Reserved 0x00000000 | Total num flows (uint32) [1 . . . 2000] | Wells in region (uint32) [1 . . . 2500] |
| Well Result Sub-Packets (see Table 5) | | Well sub-packet . . . Well sub-packet . . . | | |
| Pad DMA Packet | | 0xFFFFFFFFFFFFFFFFFFFFFFFF . . . 0xFFFFFFFFFFFFFFFFFFFFFFFF | | |

TABLE 5

| bits | 127  96 | 95  64 | 63  32 | 31  0 |
|---|---|---|---|---|
| Header | Path Metric (float32) [0.0f..511.998f] | Sequence Length # bases called (uint32) [0 . . . 4000] | Sub-Packet Size # 128b words (uint32) [1 . . . 2251] | Well ID (uint32) |
| Base Sequence | | Base[15] ASCII [A\|C\|G\|T] Base[0] (16 × uchar8) . . . (Pad 0 × 00) (Pad 0 × 00), Base[SeqLen-l] Base[SeqLen-n] | | |
| Prediction Values | Predict[3] (float32) | Predict[2] (float32) | Predict[1] (float32) | Predict[0] (float32) |
| | Pad 0 × 00000000 (0.0f) | Pad 0 × 00000000 (0.0f) | . . . Predict [flows-1] (float32) | Predict[flows-2] (float32) |
| Residual Values | Residual[3] (float32) | Residual [2] (float32) | Residual[1] (float32) | Residual [0] (float32) |
| | Pad 0 × 00000000 (0.0f) | Pad 0 × 00000000 (0.0f) | . . . Residual[flows-1] (float32) | Residual [flows-2] (float32) |
| Normalizer Gains | Gain[3] (float32) | Gain[2] (float32) | Gain[1] (float32) | Gain[0] (float32) |
| | Pad 0 × 00000000 (0.0f) | Pad 0 × 00000000 (0.0f) | . . . Gain[flows-1] (float32) | Gain[flows-2] (float32) |
| Normalizer Offsets | Offset[3] (float32) | Offset[2] (float32) | Offset[1] (float32) | Offset[0] (float32) |
| | Pad 0 × 00000000 (0.0f) | Pad 0 × 00000000 (0.0f) | . . . Offset[flows-1] (float32) | Offset[flows-2] (float32) |

According to various embodiments and as will be described in greater detail hereinbelow, the hardware and data architecture described above provides a highly parallelizable implementation of a basecalling processor. The computational workflow my extend or replace existing algorithms, including for example, the Treephaser model for predictive basecalling described in Sikora et al., U.S. Patent Application Publication Nos. 2013/0060482 and 2013/0090860.

According to various embodiments, the basecall processor 1100 including the normalize and solve pipeline 1170, get best child module 1175, loop control module 1165, well buffer 1160, and input/output control modules 1150, 1155 may be adapted to use the parallel treephaser methods described below. Advantageously, batch-processing methods may be leveraged for a group of wells corresponding to sample signal data that share a common set of phasing and normalization parameters. In various embodiments, these wells may be located in suitable proximity to one another to utilize carry forward/incomplete extension parameters (CAFIE) calculated in accordance with the methods described in PCT Patent Application Serial No. PCT/US2007/004187 and U.S. Pat. No. 8,364,417, the contents of which are hereby incorporated by reference in their entirety.

In various embodiments, the aforementioned hardware-embedded basecall processor enables highly parallelized nucleotide identification from sequencing signal data. Enhanced performance is further attained at least in part by configuring the computational pipeline for single pass parsing of treephasing analysis. As a result, execution time is improved to depend on read length rather than multiple iterations of a conventional computational approach.

Figure 12:
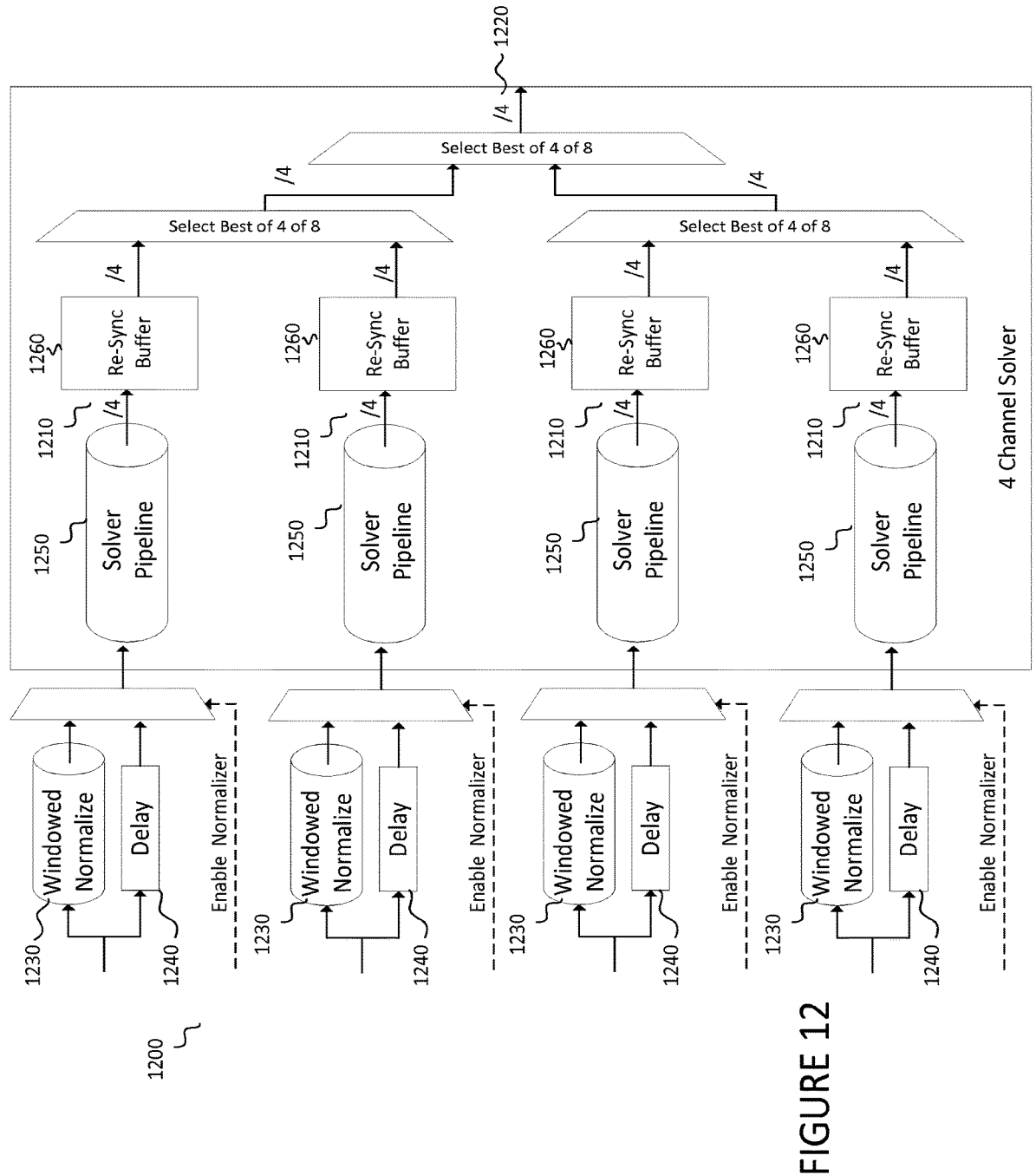
FIG. 12 illustrates an embodiment of a hardware-enabled normalize and solve pipeline according to the present disclosure.

For example, as shown in FIG. 12 sixteen candidate basecall paths 1210 (indicated in groupings of four by "/4") may be generated for each basecall estimate iteration with the four candidates 1220 retained for the next iteration. Extending candidate paths in parallel desirably provides for improved or fairer comparisons of potential basecall as the paths are at the same length and roughly the same depth. In various embodiments, branching and pruning of candidate paths may be performed in a manner similar to that for existing methods such as those referenced above relating to a "treephaser" basecalling approach.

According to various embodiments, extending candidate paths in parallel as described above provides for an improved or fairer comparison of the putative basecalls for any candidate base in the nucleotide sequence relative to conventional methods as the basecall paths are generally of the same length and depth. In determining selected basecall paths to pursue during the analysis, branching and pruning of putative basecalls may occur under similar conditions as described for conventional methods (see aforementioned references for additional details). Improvements in performance may further be realized by trimming or excluding low probability base prediction branches. In conventional approaches, such low probability base prediction branches are often reached towards the end of the tree and are time consuming to process without markedly changing the overall analysis results. According to the present disclosure, such inefficient base prediction tree traversal paths may be desirably avoided as they are not be reached by the basecall processor at least in part as they may be excluded from top candidate basecalls through earlier paths.

In various embodiments, idle time between basecalling iterations is desirably avoided while the sequencing signal data makes its way through the basecall processing pipeline. In one aspect, idle time can be desirably avoided by modification of the basecaller architecture to interleave multiple well buffers 1160 thereby making improved use of potential idle time.

FIG. 12 illustrates an embodiment of a normalize and solve pipeline 1200 for basecall analysis implemented on the hardware-enabled basecall processor 1020 according to the present disclosure. As described above, implementing a sequencing signal processing workflow in a dedicated-hardware processor such as an FPGA or GPU provides significant performance advantages relative to conventional basecall algorithms coded in high-level languages (e.g. C, python, java, etc.) executed on standard computing platforms and operating systems. In one exemplary application, the basecall processor 1020 may be configured for receiving and processing data from one or more types of sequencing instruments.

In various embodiments, the basecall normalize and solve pipeline 1200 may be implemented as one or more windowed normalizers 1230. The windowed normalizers 1230 may be configured as data containers each holding a particular basecall hypothesis that will be evaluated by the normalize and solve pipeline 1200. This approach extends the basecalling methodology providing multiple parallel channels (for example four distinct channels) where each channel processes a discrete base identification hypothesis to be tested. Data normalization may take place each cycle where the normalize function operates to smooth gain and offset errors to improve confidence in the ultimate basecall.

In various embodiments, the windowed normalizer methods improve overall basecalling by dynamically addressing gain and offset median values during each cycle of the analysis. Normalization of the data in this manner is beneficially provided without a substantial time penalty relative to conventional basecalling methods by applying a streaming or single-pass approximation for potential errors in the data rather finding an exacting solution. In this regard, conventional solving techniques are highly iterative and consequently time and computing resource intensive.

One or more delay elements 1240 may further be included in parallel with the normalizers 1230 as shown. The delay element 1240 may delay the sequencing signals used by the normalize and solve pipeline 1170 that are not required to pass through the normalizer 1230. The delay may further be used to bypass sequencing signals that may pass through the normalizer 1230. One example of such a pass-through may occur when there are not yet enough predictions to fill the first windowed normalization. In various embodiments, each of the four input paths are independently controlled to allow activations at different times depending on the predicted base sequence lengths. When the normalizers 1230 have been enabled, the sequencing data may be re-normalized substantially each iteration helping to ensure that the data being extended is as accurate.

In various embodiments, one or more solver pipelines 1250 extend the sequence (for example, by one base) in a manner similar to the previous example shown in connection with FIG. 8 however the solver pipelines 1250 are configured to simultaneously calculate multiple base extension predictions. For example, each of the four possible extensions may be calculated simultaneously rather than executing four iterations of the same loop. It will be appreciated that many of the calculation steps are common between the four bases and as such a great deal of calculation effort is conserved by extending all four bases in parallel and only replicating the code for the base specific differences. Finally, each solver pipeline 1250 may be configured to output four streams 1210 each representative of a possible base extension.

In various embodiments, the latency through each solver pipeline 1250 varies slightly and may depend on the phasing window parameters and updates thereto. Consequently, one or more re-sync buffers 1260 may be configured to re-align the data streams 1210 associated with the "select best four paths." In various embodiments, selected candidate paths (for example the top four paths) are passed back to the well buffer 1060 while others are excluded and/or discarded.

In various embodiments, where there are less than four input paths or not all of the output paths are valid, the unused paths are marked as unused by a "valid" flag. This flag may serve as a parameter to prevent downstream modules from using the results of these paths to avoid unnecessary computational load and erroneous outputs. In various embodiments, the final output stage of the pipeline pushes a "zero" data set to the well buffer 1060 on a given channel when it is marked as "invalid", to aid in initialization of a known state for the next iteration.

Figure 13:
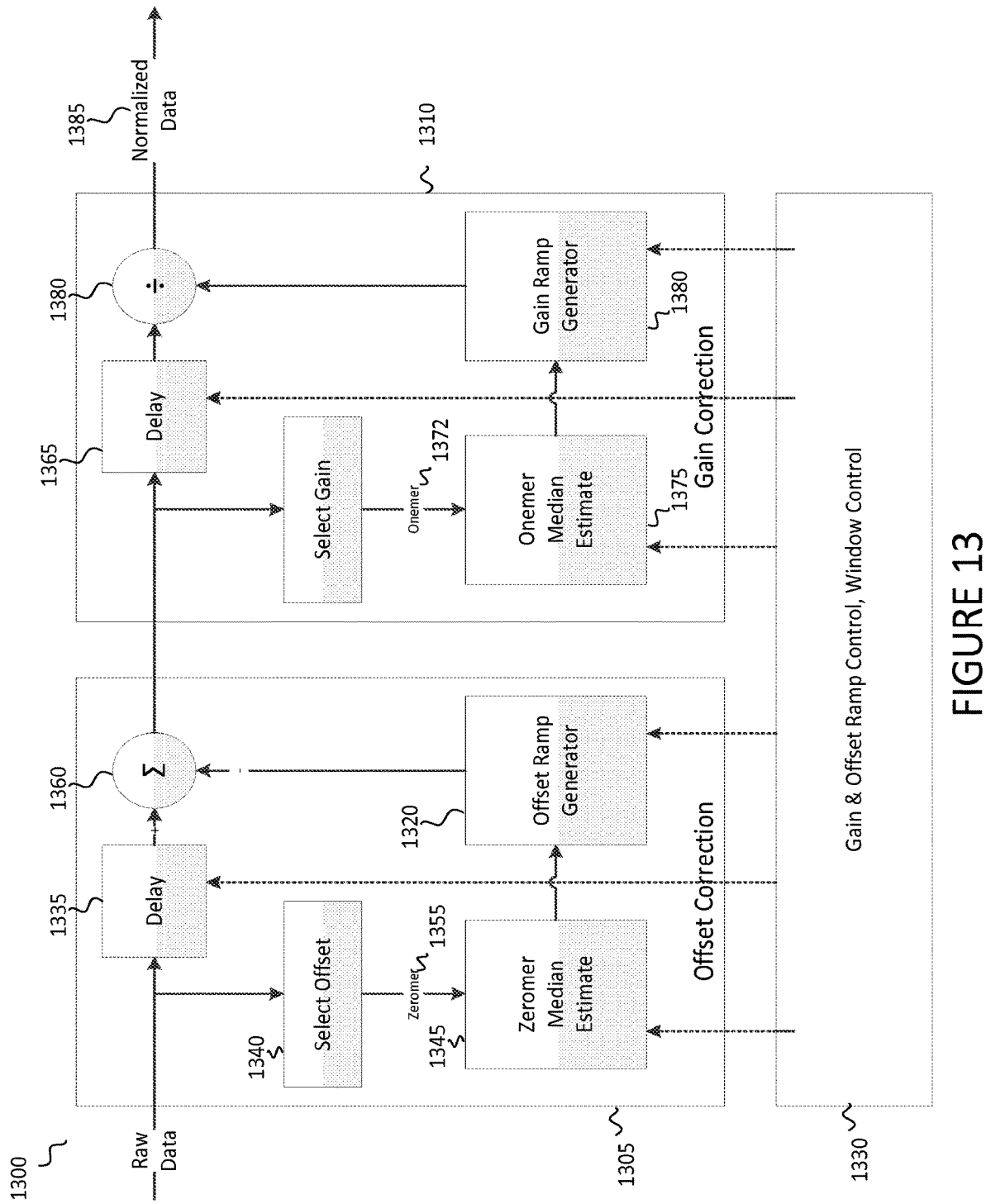
FIG. 13 further details exemplary logic for a windowed normalizer associated with the normalize and solve pipeline according to the present disclosure.

FIG. 13 further details exemplary logic for a windowed normalizer 1300 associated with the normalize and solve pipeline 1200 according to the present disclosure. In various embodiments, the windowed normalizer 1300 implements a parallel solving functionality for base identification adapted from methods described above with respect to "treephasing" methods. The computational efficiency of the windowed normalizer 1300 is improved by the aforementioned flow of the analysis that may modified and optimized for single-pass non-iterative streaming to reduce latency. A notable advancement in the implementation of the windowed normalizer 1200 of the present disclosure relates to the determination of base signal median estimates. Rather than applying an iterative median calculation, the windowed normalizer 1300 of the present disclosure applies as a sliding window approximation approach. According to this method, the median approximation is reset at the start of each normalization window avoiding potential drift in the data that may occur.

In various embodiments, the windowed normalizer 1300 comprises an offset correction component 1305 and a gain correction component 1310. The offset correction component 1305 and gain correction components 1310 are further controlled by a controller 1330. The offset correction component 1305 receives sequence signal data (e.g. raw data) and a copy of the data is made by a delay component 1335. The delay component 1135 further processes a latency associated with the offset calculation and is responsive to signals triggered by the controller 1330. A select offset component 1340 receives the sequence signal data and a zeromer media estimate component 1345 implements functionality for generating a running median that may be latched by an offset ramp generator 1350 as instructed by the controller 1330. Zeromer basecall estimates 1355 result in a zero offset by the offset correction component 1305. The summing junction "s" 1360 subtracts the stream of offset values from the stream of delayed data, generating offset corrected data 1362 ready for gain correction by the gain correction component 1310.

A delay block 1365 of the gain correction component 1310 receives the offset corrected data 1362 and delays it by the processing latency for the gain calculation with the delay being triggered by the control block 1330.

For a selected gain 1370, a onemer median estimate component 1375 operates in a manner similar to the zeromer median estimate 1345. Upon receiving onemer data 1372, the onemer media estimate 1375 may default to a value of 1.0 (e.g. unity gain) in the absence of valid input data. The output of the onemer media estimate 1375 is latched by a gain ramp generator 1380 when instructed to do so by the controller 1330. The gain ramp generator 1380 produces a stream of gain corrected values (similar to the concept applied for the offset ramp generator 1320). Finally, the pipelined divider "÷" 1380 divides the stream of delayed offset corrected data by the corresponding gain correction values and a stream of normalized data 1385 may be output from the windowed normalizer 1300.

Figure 14:
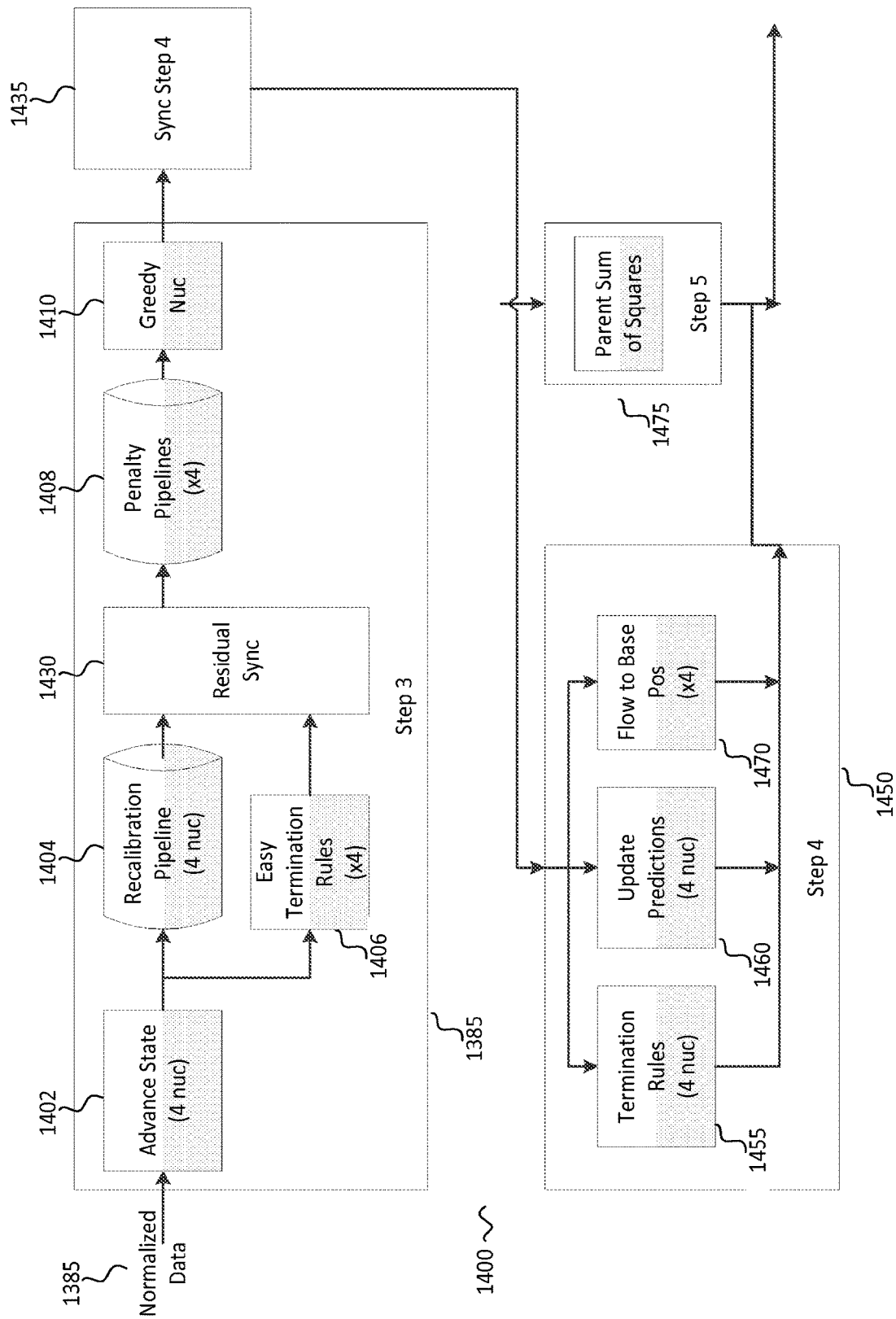
FIG. 14 further details exemplary logic for a solver associated with the normalize and solve pipeline according to the present disclosure.

FIG. 14 further details exemplary logic for a solver 1400 associated with the normalize and solve pipeline 1200 according to the present disclosure. The solver 1400 provides for a highly parallelized linear data flow that may be implemented for example using a FPGA or GPU processor. In various embodiments, the solver 1400 maintains consistency in the data flow keeping each data stream in sync with one another and aligns the data according to the bit fields discussed above improving the efficiency of the analysis.

In various embodiments, the solver 1400 is implemented as parallel data paths and execution steps are executed in parallel as practical to minimize or reduce latency. Delay elements may further be used to align the results for each of the nucleotide basecall estimates so that result comparisons may be made between the data streams. Such an approach may improve speed and efficiency of the systems by avoiding storing data and results in RAM (a slower and less efficient operation).

In the solver 1400, data streams are periodically re-aligned by sync operators 1430, 1435 providing the ability to share resources. Synchronization blocks 1430, 1435 may be optional but desirably implemented as an alternative to replicating shared resources.

For each iteration of the solver 1400, a main solver block 1415 includes processing logic steps 1402, 1404, 1406, 1408, and 1410 that are executed on incoming normalized data 1385. In various embodiments, processing may occur even where a nucleotide path has reached a termination condition as it may be more efficient to continue the process and discard the result than to implement additional gating and delay logic to balance the pipelines.

An advance state function 1402 implements processes each of the four nucleotide calls substantially simultaneously, where the majority of processing is common. Four output data streams are thus generated, each extending the supplied input stream by the corresponding basecall.

If enabled, a recalibration pipeline 1404 applies recalibration coefficients to the four data streams before calculating the residual values. A test for easy termination 1406 comprises one or more termination rules applied to the four data streams from advance state 1402. In various embodiments, various flags may be set indicating the status of whether certain termination criteria have been met or not. In various embodiments, this functionality 1402 is independent of the recalibration pipeline and executes in parallel.

A residual sync block 1430 synchronizes the four data streams and readies the data for a greedy nucleotide calculation as discussed in connection with the treephaser analysis methods by aligning the data. A series of four penalty pipelines 1408 implement metric and penalty calculations. Thereafter, a greed nucleotide block 1410 performs the greedy nucleotide calculation and selects the best basecall. The greedy nucleotide block further passes through additional stream and state information produced by the penalty pipelines 1408.

The sync step 4 block 1435 re-aligns the data streams ready for "step 4" block 1450 and "step 5" block 1475 processing. Processing in the step 4 block 1435 applies one or more termination rules 1455 to each of the basecall paths simultaneously. Update predictions 1460 generates an output sequence stream for the data to be further processed by the flow to base functionality 1470. Step 5 block 1475 determines the sum_of_squares value for the parent basecall prediction path using the re-normalized data. The parent data may also be re-calibrated as desired. Step 5 block 1475 is calculated in parallel to step 4 block 1450 as the two operations can be executed independently of each other.

Figure 15:
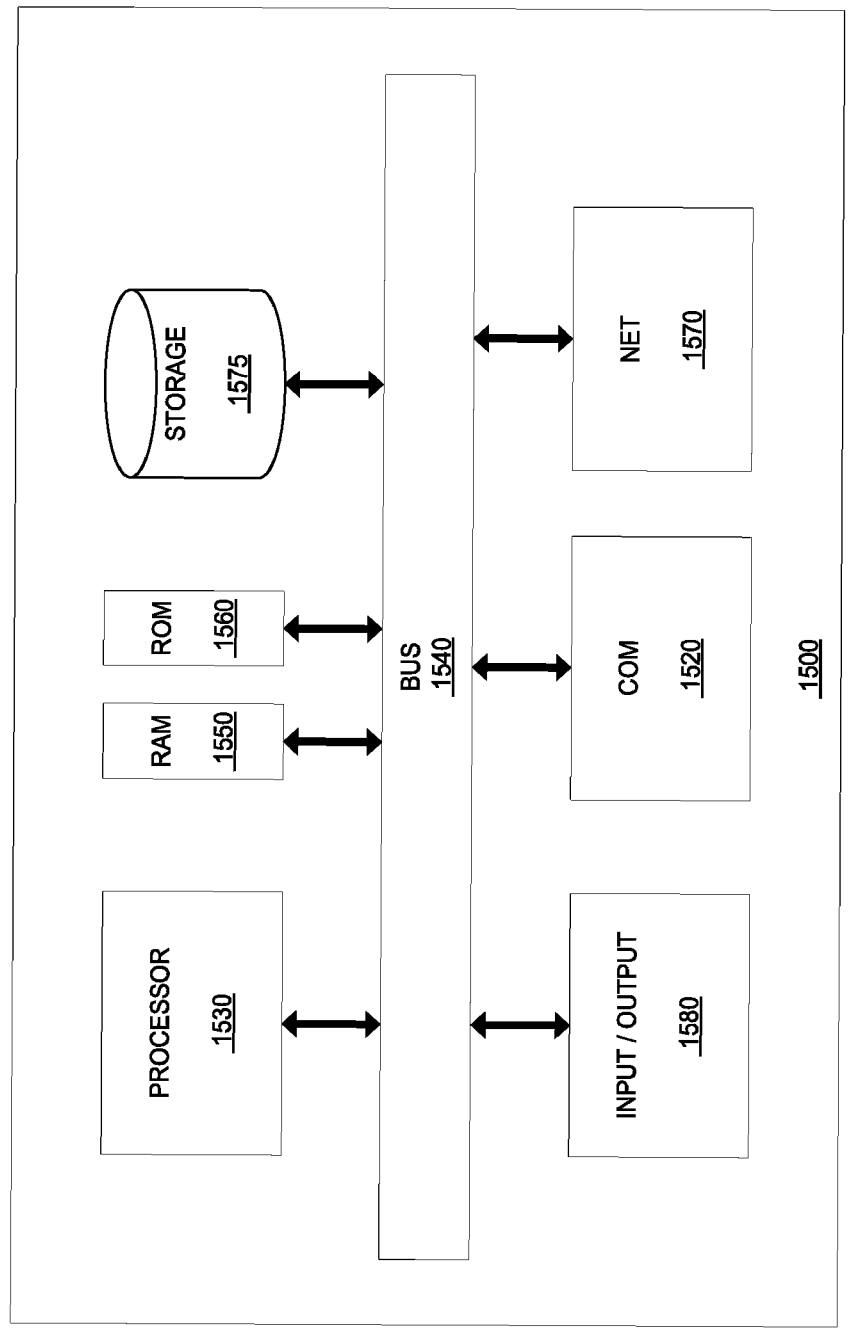
FIG. 15 is a block diagram of a computer, system, and/or server for executing the methods described according to exemplary embodiments of the present disclosure.

FIG. 15 is a simplified functional block diagram of a computing environment 1500 that may be configured as a computer, system, and/or server for executing the methods described above, according to an exemplary embodiment of the present disclosure. Specifically, in one embodiment, any of computers, systems, and/or servers implementing the above-described disclosure may be an assembly of hardware including, for example, a data communication interface 1520 for packet data communication. The platform may also include a processing unit, FPGA, GPU, CPU, etc. 1530, in the form of one or more processors, for executing program instructions. The platform typically includes an internal communication bus 1540, program storage 1575, and data storage for various data files to be processed and/or communicated by the platform such as RAM 1550 and ROM 1560, although the system 1500 often receives programming and data via network communications 1570. The computing environment 1500 also may include input and output ports 1580 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While the presently disclosed application, methods, computers, servers, devices, and systems are described with exemplary reference to computer applications and to transmitting various types of data, it should be appreciated that the presently disclosed embodiments may be applicable to any environment, such as a desktop or laptop computer, etc. Also, the presently disclosed embodiments may be applicable to any type of Internet protocol that is equivalent or successor to HTTP.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for sample nucleotide sequence determination comprising:
    a sensor array adapted for sequencing, the sensor array including a plurality of wells containing sample polynucleotides and configured to receive a plurality of flows of nucleotides flowed in a flow order;
    a signal data processor that receives signal data from the sensor array, the signal data resultant from chemical reactions associated with the flow of nucleotides, the signal data comprising a plurality of signal samples corresponding to the plurality of wells of the sensor array, wherein an input packet structure is configured to store the plurality of signal samples, the input packet structure including a bit field for each signal sample, a well identification bit field, a flow order identification bit field and a parameter bit field;
    a basecall processor that receives signal data from the signal data processor by accessing the plurality of signal samples from the input packet structure for a given well, the basecall processor including a well buffer to store the plurality of signal samples for the given well and a plurality of parallel processing channels, wherein each parallel processing channel is operable to test a particular nucleotide identification hypothesis that differs from each of the other processing channels, wherein each processing channel provides a putative basecall simultaneously with the other processing channels to produce a plurality of putative basecalls, wherein the basecall processor selects from the plurality of putative basecalls a resulting nucleotide identification basecall with a highest confidence of being attributable to a given nucleotide flow; and a data output module that assembles the resulting nucleotide identification basecalls in an output packet structure, the output packet structure including a sequence length bit field, a base bit field for each nucleotide identification basecall and a second well identification bit field and outputs an identified nucleotide sequence for the sample polynucleotide.

2. The system of claim 1, wherein the plurality of parallel processing channels of the basecall processor is configured to process the nucleotide identification hypotheses in groupings of four parallel processing channels, one for each nucleotide G, A, T, C of the flow order.

3. The system of claim 2, wherein the groupings of four parallel processing channels are further coupled to process sixteen nucleotide identification hypotheses in parallel of which four putative basecalls are retained and processed in a next iteration of the basecall processor.

4. The system of claim 1, wherein each processing channel applies a single-pass, non-iterative approximation of a gain and an offset to apply to the signal samples.

5. The system of claim 4, wherein the output data packet further includes a gain bit field and an offset bit field to store the gain and the offset.

6. The system of claim 1, wherein the basecall processor comprises a graphics processing unit or a field programmable gate array.

7. The system of claim 1, wherein the basecall processor further comprises a direct memory access (DMA) interface comprising a DMA receiver configured to receive the input packet structure.

8. The system of claim 1, wherein the basecall processor further comprises a direct memory access (DMA) interface comprising a DMA transmitter configured to transmit the output packet structure.

9. The system of claim 1, wherein the basecall processor is configured to operate using an independent clock.

10. The system of claim 1, wherein the output data packet further includes predicted data value bit fields to store predicted data values generated by the basecall processor.

11. The system of claim 1, wherein the output data packet further includes residual value bit fields to store residual values generated by the basecall processor.

12. A sequence determination apparatus comprising:
a basecall processor that receives signal data from a sequencing instrument and identifies putative basecalls corresponding to a nucleotide sequence for a sample polynucleotide contained in a plurality of wells of a sensor array associated with the sequencing instrument, wherein the signal data result from chemical reactions that take place for a plurality of flows of nucleotides into the plurality of wells during sequencing on the sequencing instrument, wherein the nucleotides are flowed in a flow order, wherein the signal data comprise a plurality of signal samples corresponding to the plurality of wells of the sensor array, wherein an input packet structure is configured to store the plurality of signal samples, the input packet structure including a bit field for each signal sample, a well identification bit field, a flow order identification bit field and a parameter bit field, wherein the basecall processor accesses the plurality of signal samples from the input packet structure for a given well, the basecall processor including a well buffer to store the plurality of signal samples for the given well;

a plurality of parallel processing channels implemented as a plurality of logic gates within the basecall processor, each parallel processing channel comprising: (a) a normalization component corresponding to a given nucleotide identification hypothesis that applies a gain and an offset to the signal data to generate normalized signal data, (b) a solver component applied to the normalized signal data that identifies a putative basecall corresponding to the normalized signal data, and (c) a best candidate selector that generates a resulting nucleotide identification basecall with a highest confidence of being attributable to a given nucleotide flow; and a data output module that assembles the resulting nucleotide identification basecalls in an output packet structure, the output packet structure including a sequence length bit field, a base bit field for each nucleotide identification basecall and a second well identification bit field and outputs an identified nucleotide sequence for the sample polynucleotide.

13. The apparatus of claim 12, wherein the plurality of parallel processing channels of the basecall processor is configured to process the nucleotide identification hypotheses in groupings of four parallel processing channels, one for each nucleotide G, A, T, C of the flow order.

14. The apparatus of claim 13, wherein the groupings of four parallel channels are further coupled to process sixteen nucleotide identification hypotheses in parallel of which four putative basecalls are retained and processed in a next iteration of the basecall processor.

15. The apparatus of claim 12, wherein the basecall processor comprises a graphics processing unit or a field-programmable gate array.

16. The apparatus of claim 12, wherein the basecall processor further comprises a direct memory access (DMA) interface comprising a DMA receiver configured to receive the input packet structure.

17. The apparatus of claim 12, wherein the basecall processor further comprises a direct memory access (DMA) interface comprising a DMA transmitter configured to transmit the output packet structure.

18. The apparatus of claim 12, wherein the basecall processor is configured to operate using an independent clock.

19. The apparatus of claim 12, wherein the output data packet further includes a gain bit field and an offset bit field to store the gain and the offset.

* * * * *

SEQUENCE LISTING

<160> NUMBER OF SEQ ID NOS: 2

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttttttttt                                                            10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcagttgact                                                           10